United States Patent [19]

Beecher

[11] Patent Number: 4,889,533

[45] Date of Patent: Dec. 26, 1989

[54] FEMALE URINARY COLLECTION DEVICES HAVING HOLLOW-WALLED FILLED URINE RECEPTACLES

[76] Inventor: William H. Beecher, 292 Boyd Ave., Elmhurst, Ill. 60126

[21] Appl. No.: 868,292

[22] Filed: May 28, 1986

[51] Int. Cl.$^4$ .............................................. A61F 5/44
[52] U.S. Cl. ................................................... 604/330
[58] Field of Search .............................. 604/327–331, 604/353, 386, 391; 4/144.1–144.4; 128/129, 761, 767, 768; 277/226, 227

[56] References Cited

U.S. PATENT DOCUMENTS

| | | |
|---|---|---|
| 976,883 | 11/1910 | Keagy et al. |
| 2,365,296 | 12/1944 | Schimpf .............................. 128/129 |
| 2,483,079 | 9/1949 | Williams . |
| 3,072,125 | 1/1963 | O'Brien . |
| 3,335,714 | 8/1967 | Giesy . |
| 3,520,305 | 7/1970 | Davis . |
| 3,528,423 | 9/1970 | Lee . |
| 3,683,914 | 8/1972 | Crowley . |
| 3,721,243 | 3/1973 | Hesterman et al. . |
| 3,776,235 | 12/1973 | Radcliffe et al. . |
| 3,804,094 | 4/1974 | Manoussos et al. . |
| 3,815,581 | 6/1974 | Levin . |
| 3,931,819 | 1/1976 | Weedle . |
| 3,995,329 | 12/1976 | Williams . |
| 4,145,763 | 3/1979 | Abrams et al. ...................... 604/391 |
| 4,198,979 | 4/1980 | Cooney et al. . |
| 4,246,901 | 1/1981 | Frosch ................................. 604/329 |
| 4,270,539 | 6/1981 | Frosch ................................. 4/144.3 |
| 4,421,511 | 12/1983 | Steer et al. .......................... 4/144.3 |
| 4,496,355 | 1/1985 | Hall et al. . |
| 4,615,692 | 10/1986 | Giacalone et al. .................. 604/329 |

FOREIGN PATENT DOCUMENTS

| | | |
|---|---|---|
| 0018749 | 11/1980 | European Pat. Off. . |
| 2416036 | 4/1975 | Fed. Rep. of Germany . |
| 996370 | 6/1965 | United Kingdom . |
| 2070936 | 9/1981 | United Kingdom . |
| 2090144 | 7/1982 | United Kingdom ................ 604/331 |
| 2126902 | 4/1984 | United Kingdom ................ 604/330 |

OTHER PUBLICATIONS

Product Information Sheet, Dow Corning Q7-2218 Silicone Gel System, Medical Materials, Dow Corning Corporation, Midland, Mich. 48640

(List continued on next page.)

*Primary Examiner*—J. L. Kruter
*Attorney, Agent, or Firm*—Burmeister, York, Palmatier, Zummer

[57] ABSTRACT

The disclosed device comprises a cup-shaped receptacle for collecting urine from the orifice of the female user's urethra. Such receptacle has a bottom wall portion and an annular side wall portion projecting upwardly therefrom and terminating in a soft rounded compliant annular lip portion for sealing engagement with the user's external vestibular tissues around such orifice. A drain tube portion connects with the bottom wall portion. The side wall portion is hollow and comprises spaced inner and outer shells merging at thier upper extremities to form such rounded lip portion. The inner and outer shells, including the lip portion, are made of a thin highly flexible compliant silicone elastomer or other similar material. The space between the inner and outer shells is filled with a viscous liquid silicone elastomer gum or gel, or other similar material, enabling such lip portion to conform precisely with the exact contours of the user's vestibular tissues, with a minimum of pressure between such lip and such tissues. The bottom wall portion of such receptacle preferably comprises a laterally projecting bottom flange for engaging the user's external labia majora tissue portions. The device also preferably comprises a soft flexible pessary member mounted on such bottom flange portion for insertion into the user's vagina to stabilize the position of the receptacle. The pessary member may be detachable form the device and preferably comprises a thin flexible hollow outer shell, made of a silicone elastomer or the like, and filled with a viscous liquid silicone elastomer gum or gel, so that the pessary member is extremely soft and compliant. As an alternative, the pessary member may be inflatable with air or other fluid, and also easily deflatable.

35 Claims, 15 Drawing Sheets

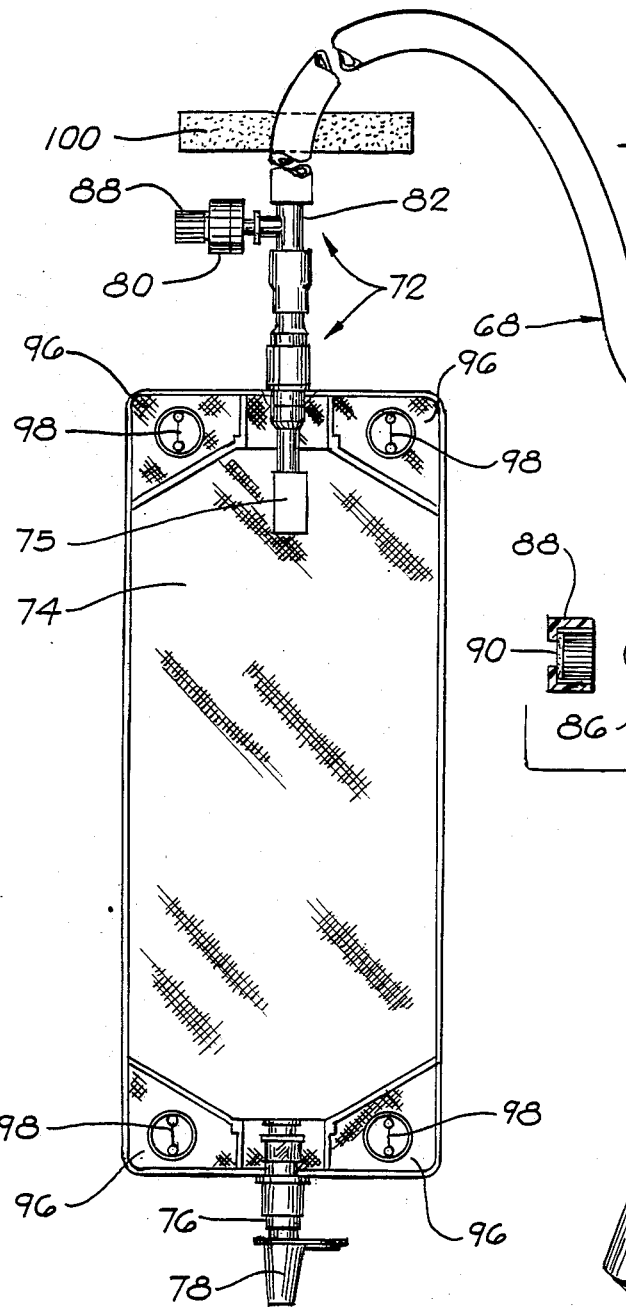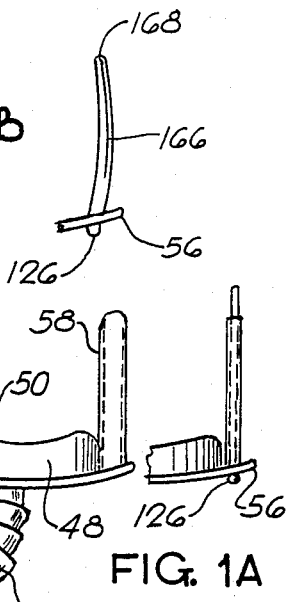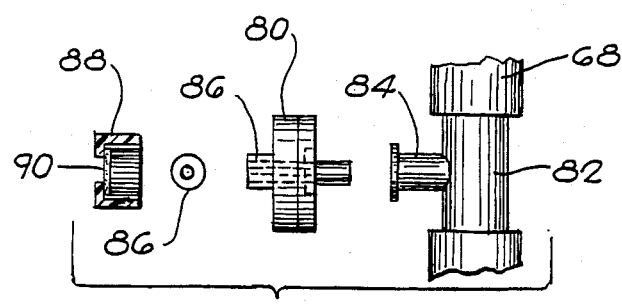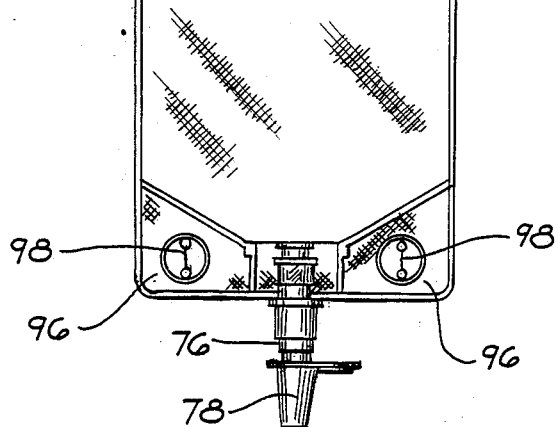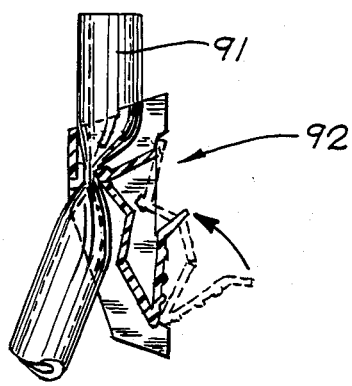

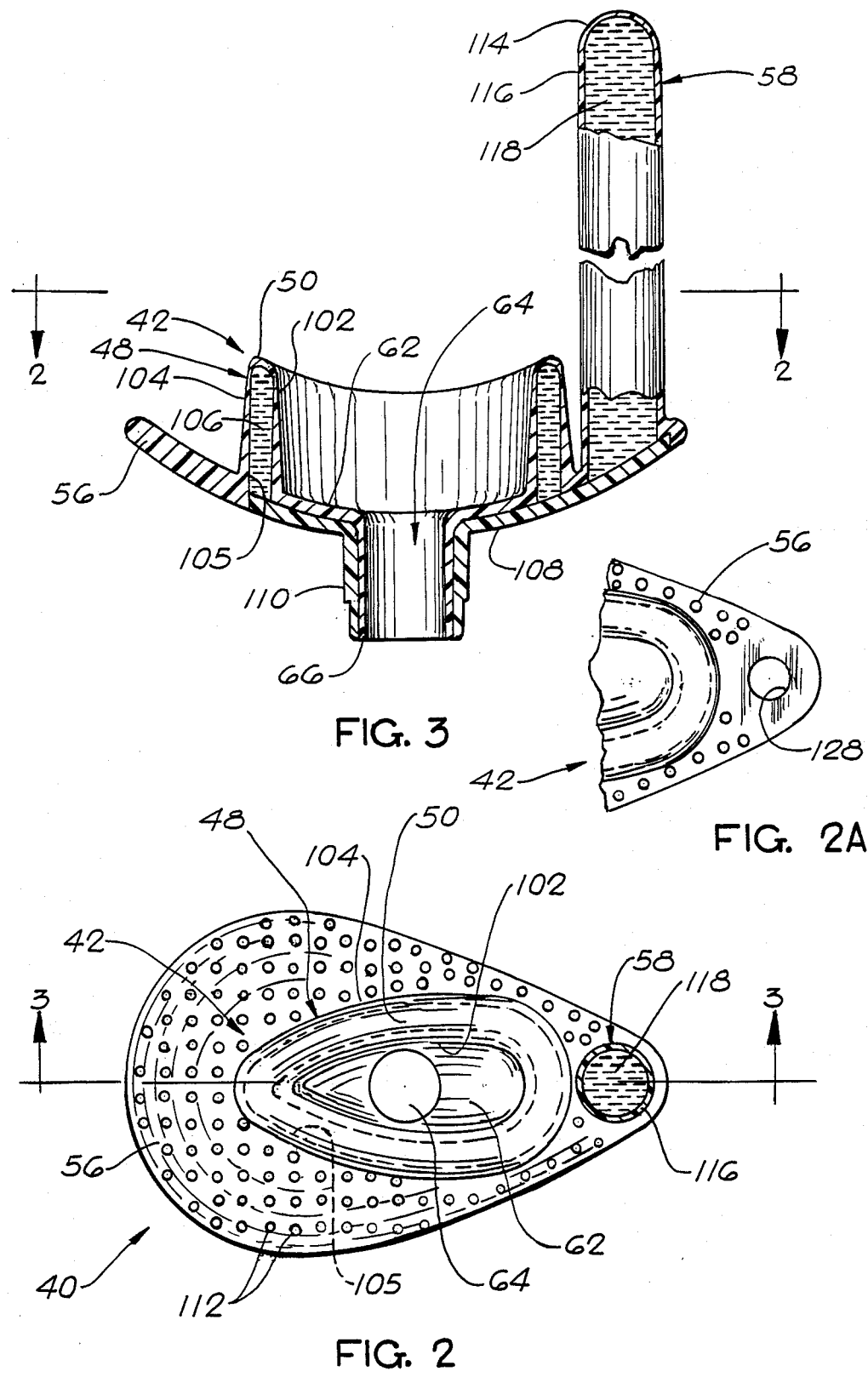

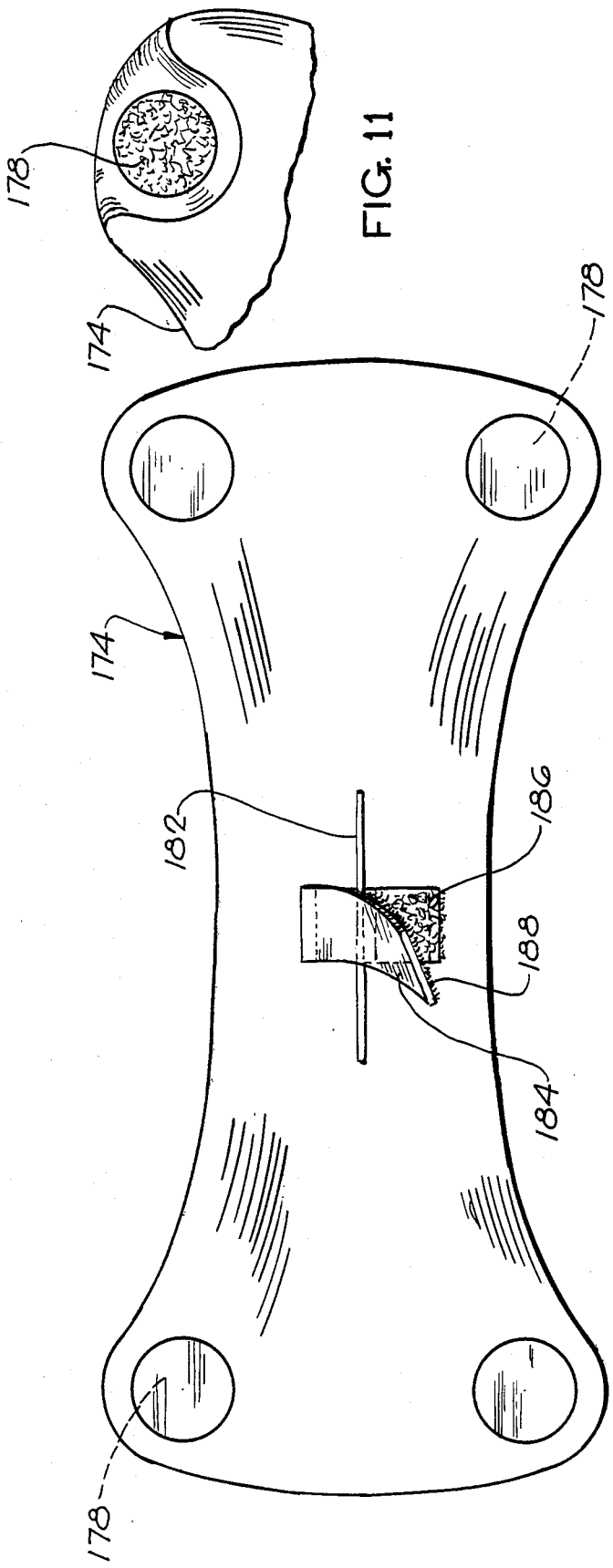

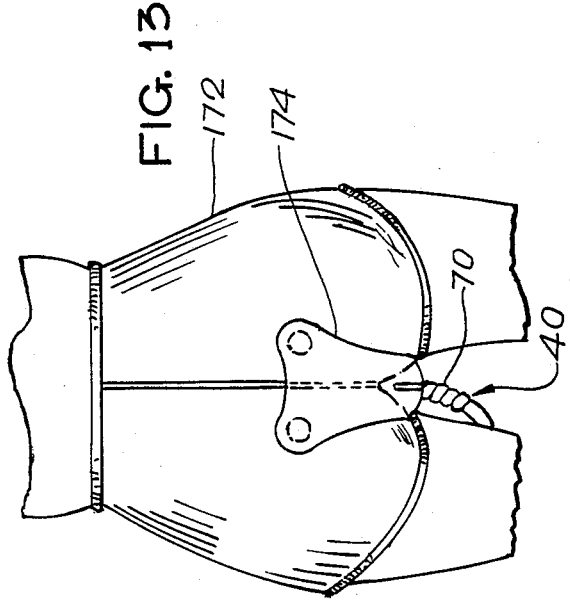
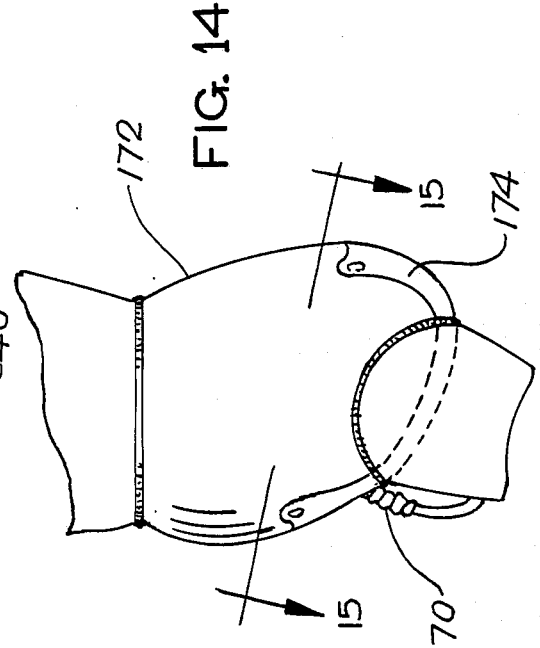
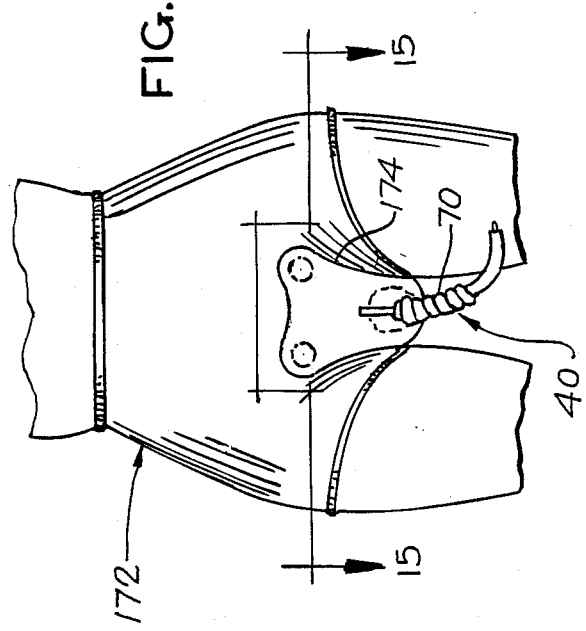
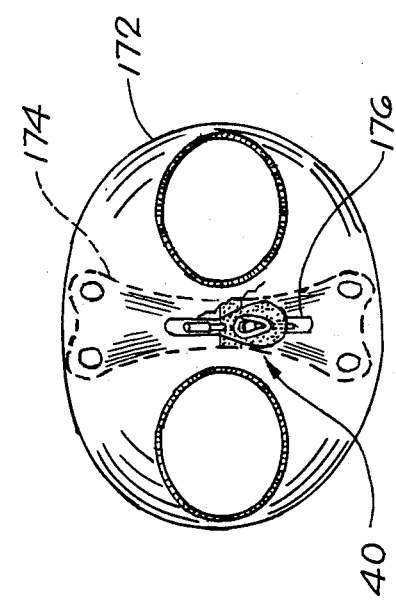

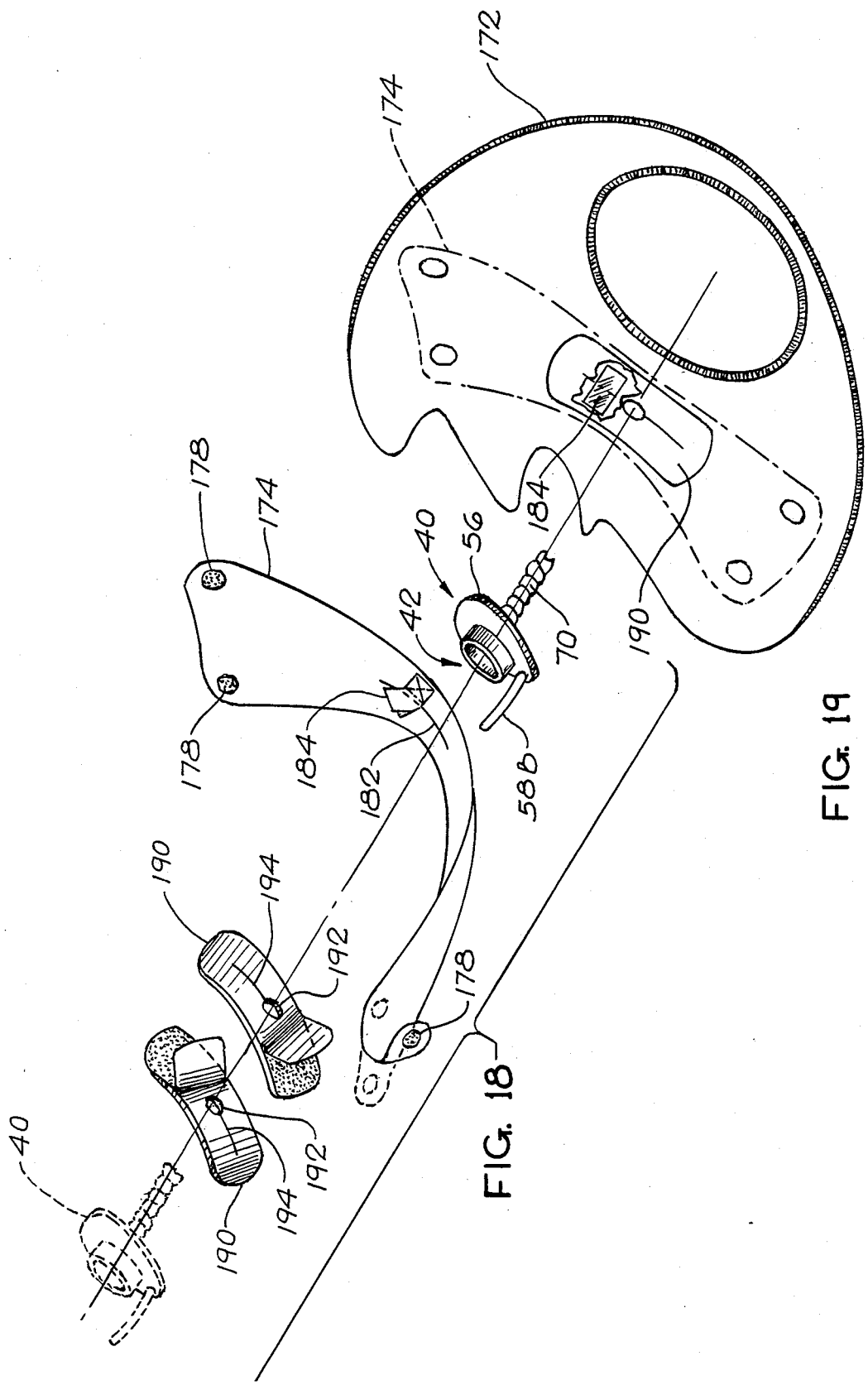

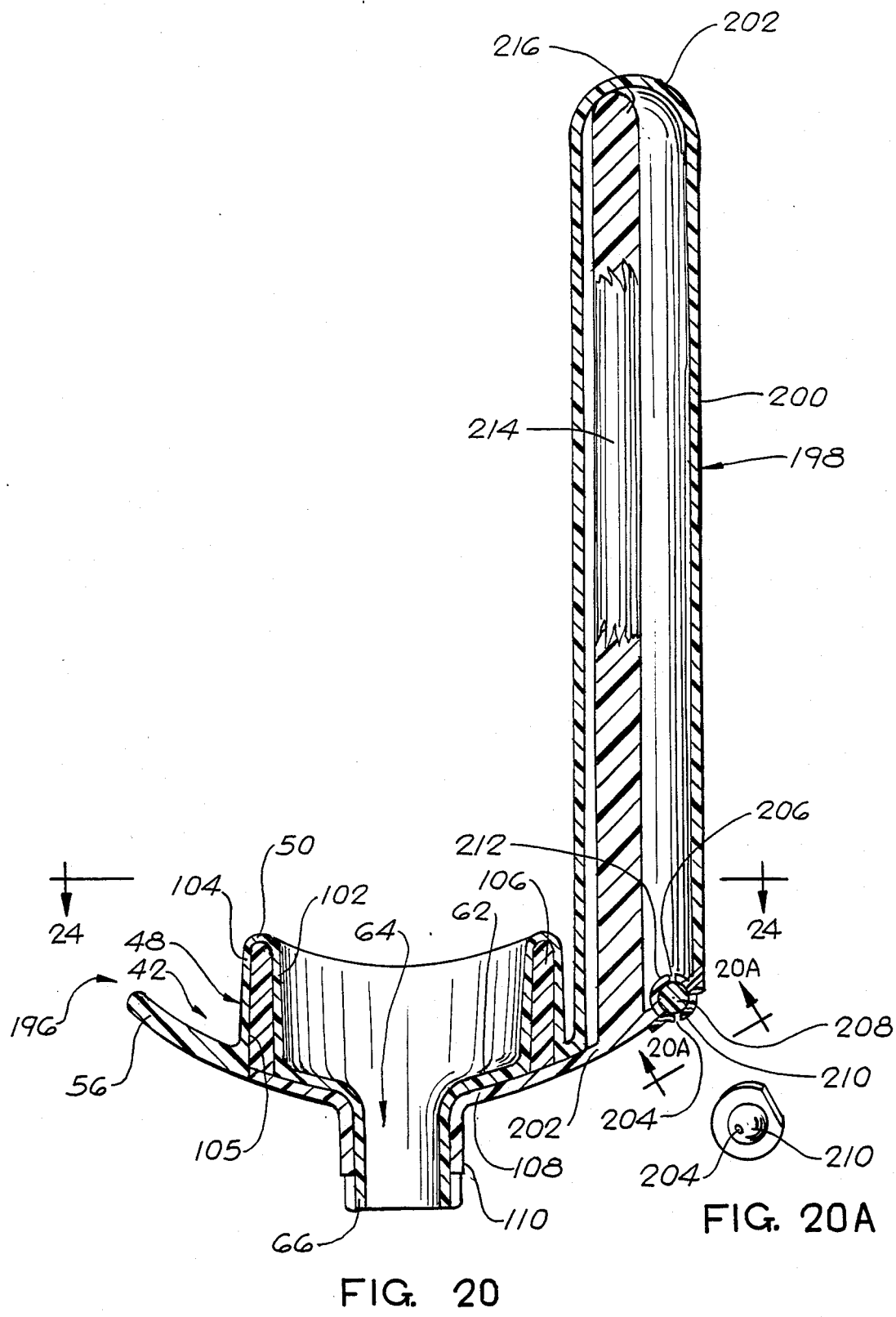

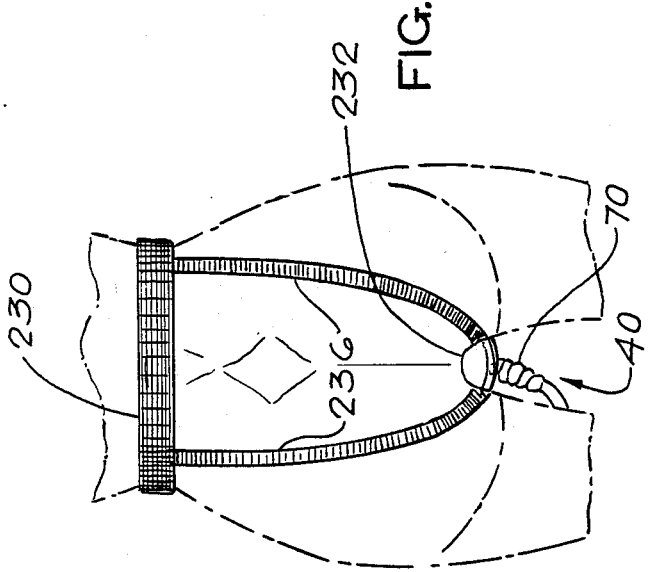
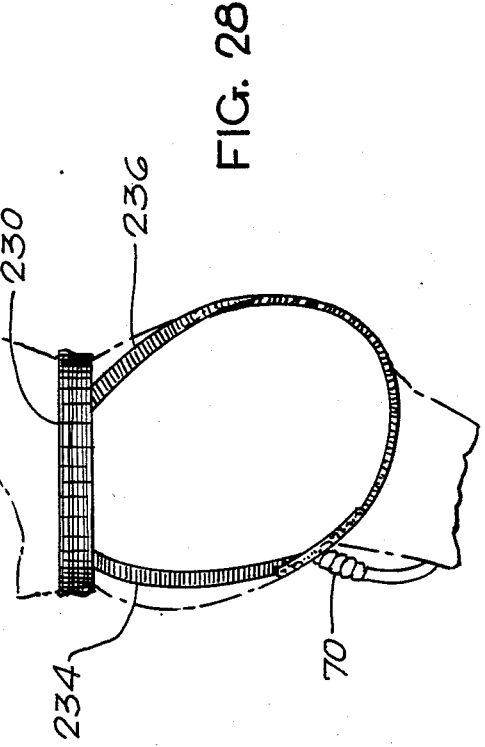
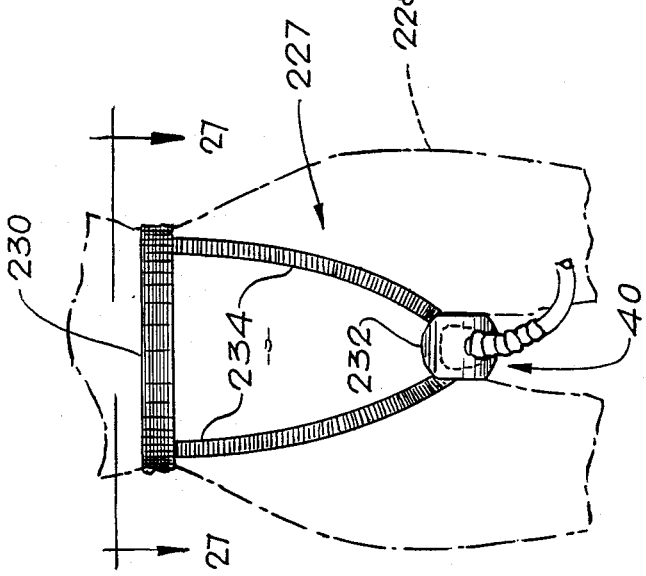
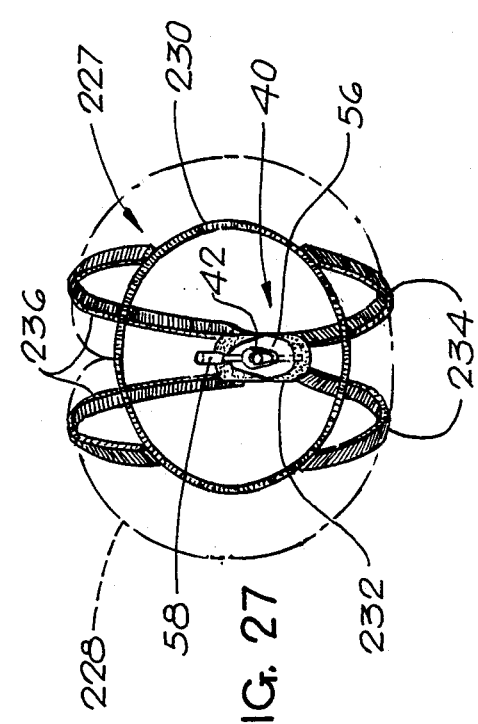

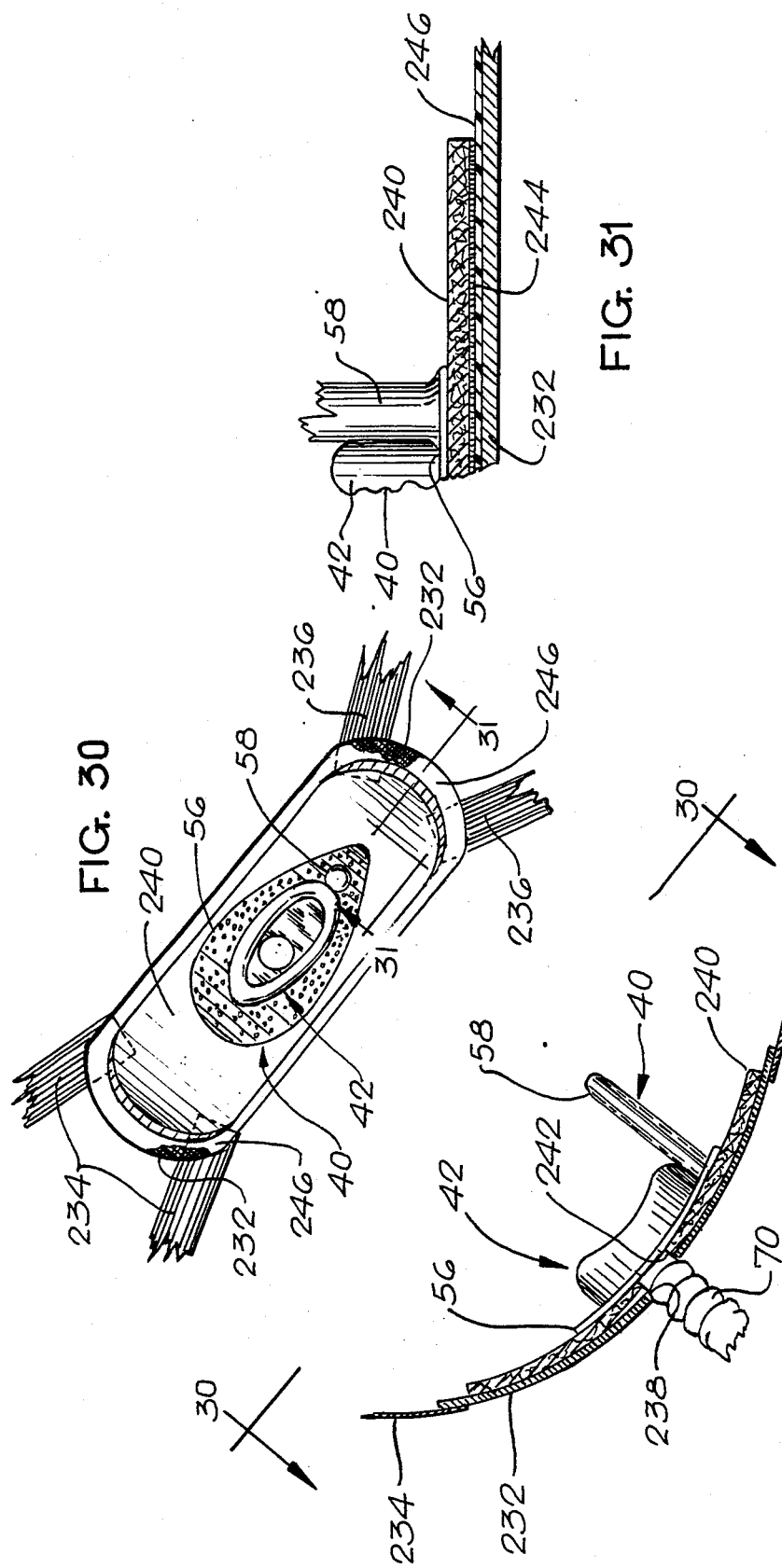

FEMALE URINARY COLLECTION DEVICES HAVING HOLLOW-WALLED FILLED URINE RECEPTACLES

FIELD OF THE INVENTION

This invention relates to urinary collection devices for use by human females, to collect urine externally, from the mouth or orifice of the urethra. There is a need for such devices by females who are incontinent, in that they are unable to contain urine on a consistent basis. A urinary collection device in accordance with the present invention is worn by a female and enables her to move about freely and to engage in virtually all normal activities.

BACKGROUND OF THE INVENTION

In the prior art, previous efforts have been made to produce female urinary collection devices. One example is disclosed in the Hall and Beecher U.S. Pat. No. 4,496,355, issued Jan. 29, 1985, and entitled EXTERNAL FEMALE URINARY APPLIANCE. Such appliance includes a generally cup-shaped receptacle which is worn by the female user so as to enclose the external orifice of the urethra. Such prior appliance has various disadvantages and problems, in that such appliance is somewhat uncomfortable to wear, and is subject to leakage of urine in some cases, due in large part to the fact that such appliance is unable to accommodate itself to the rather considerable variations in the shape of different female bodies, around the orifice of the urethra. If the pressure between such prior appliance and the female body is increased to reduce the incidence of leakage, the discomfort to the wearer is increased. Such prior appliance involves the further problem that the appliance is subject to dislocation from its intended position, in sealing engagement with the female body around the orifice of the urethra.

OBJECTS OF THE INVENTION

One object of the present invention is to provide a new and improved female urinary collection device having a receptacle with an unprecedented ability to conform itself to variations in the shape of the female body, around the orifice of the urethra, so that a perfect seal is easily and reliably achieved.

A further object is to provide such a new and improved female urinary collection device having a receptacle with an unprecedented degree of softness and compliance, so that the device can be worn with a high degree of comfort.

Another object is to provide such a new and improved female urinary collection device having exceptionally effective and comfortable means for locating and stabilizing the position of the urine receptacle around the orifice of the urethra.

SUMMARY OF THE INVENTION

These and other objects and advantages of the present invention are achieved by providing a female urinary collection device, comprising a generally cup-shaped receptacle for collecting urine from the urethra orifice of a female, such receptacle having a bottom wall portion and a generally annular side wall portion projecting generally upwardly therefrom and terminating in a soft rounded compliant generally annular lip portion for sealing engagement with the external vestibular tissues of the female around the urethra orifice, and a drain tube portion connecting with the bottom wall portion for draining the urine out of the receptacle, the side wall portion being hollow and comprising spaced inner and outer shells merging at their upper extremities to form such rounded lip portion, the inner and outer shells being made of a thin highly flexible compliant synthetic elastomer material, such side wall portion having a space between such inner and outer shells, such space being filled with a viscous liquid synthetic elastomer filling material enabling such lip to conform precisely with the exact contours of the vestibular tissues of the female around the urethra orifice with a minimum of pressure between such lip and such tissues.

The synthetic elastomer material preferably takes the form of a highly flexible compliant silicone elastomer material.

The viscous liquid synthetic elastomer filling material preferably takes the form of a silicone gum or a silicone gel.

With these materials, the side wall portion of the receptacle conforms itself precisely to the exact contours of the vestibular tissues of the female body around the orifice of the urethra, with a minimum of pressure between the rounded lip and such tissues, so that a perfect seal is established between the lip and the tissues. Moreover, the device is very comfortable to wear. When the device is removed from the body of the user, the elastomeric side wall of the device restores itself to its original shape.

Alternatively, the sealed space between the inner and outer shells may be filled with certain other fluids. Air or some other gas is advantageous in some cases. Liquids such as sterile water or normal saline solution are also good alternatives.

The urinary collection device preferably includes a bottom flange portion connecting with the bottom wall portion of the receptacle and projecting laterally therefrom for engaging the external labia majora tissue portions of the female. The bottom flange portion is also preferably made of silicone elastomer.

The urinary collection device preferably includes means wearable by the female for pressing the flange portion lightly against the external labia majora tissue portions. At the same time, the soft compliant lip portion of the receptacle is pressed lightly into sealing engagement with the external vestibular tissues of the female, around the orifice of the urethra. Such means, wearable by the female, may take the form of a belt with an elastic harness, or special elastic panties having provision for receiving and retaining the urinary collection device.

The urinary collection device may include a pessary member mounted on such flange portion of the device, for insertion into the vagina of the female, to stabilize the position of the device, so that the soft compliant lip of the receptacle will be kept in sealing engagement with the vestibular tissues around the urethra orifice.

In some cases, the pessary member includes a detachable mounting connection to the flange portion of the device, so that the device can be employed either with or without the pessary member.

The pessary member may assume various forms. In some cases, the pessary member is hollow and has a thin outer wall with a space therein, such thin outer wall being made of a flexible highly compliant synthetic elastomer material, preferably a silicone elastomer. The space is filled with a viscous liquid synthetic elastomer material, preferably a silicone elastomer gum or gel, whereby the pessary is able to conform precisely to the vaginal contours of the female.

In another construction, the pessary member is hollow and has a thin flexible compliant outer wall with a space therein, the device having inflation means for admitting a pressurized fluid to such space for inflating the pessary member after insertion into the vagina, whereby the pessary member conforms precisely to the vaginal contours of the female, with a snug retentive fit. The pessary member may include a thin stiffening member, partially occupying the space within the outer wall thereof for use in the initial insertion of the pessary member into the vagina, prior to inflation of the pessary member.

In some cases, the pessary member may have an end portion which is configured to support a tampon, adapted to be inserted into the vagina, with the pessary member.

BRIEF DESCRIPTION OF THE DRAWINGS

Further objects, advantages and features of the present invention will appear from the following description of illustrative embodiments, such description being taken in connection with the accompanying drawings, in which:

FIG. 1 is a general elevational view of a female urinary collector device, to be described as an illustrative embodiment of the present invention.

FIG. 1A is a fragmentary elevational detail, similar to a portion of FIG. 1, but showing a detachable pessary construction.

FIG. 1B is another fragmentary elevational detail, showing an alternate construction of a detachable pessary.

FIG. 2 is an enlarged plan view of a urine collection receptacle, for use in the female urinary collection device, the view being partly in section along the line 2—2 in FIG. 3.

FIG. 2A is a fragmentary view similar to a portion of FIG. 2 but showing a modified flange plate having an opening which is adapted to receive the detachable pessary of FIG. 1A.

FIG. 3 is a fragmentary elevational section, taken generally along the line 3—3 in FIG. 2.

FIG. 8 is an enlarged, exploded or disassembled view, showing a valve and filter assembly employed in the construction of FIG. 1.

FIG. 9 is an enlarged fragmentary elevational section, showing a shutoff clamp mounted on a drain hose for the device of FIG. 1.

FIG. 10 is a lower plan view of a removable crotch panel for use with elastic panties to retain the female urinary collection device on the body of the user.

FIG. 11 is a fragmentary detail, corresponding to a portion of FIG. 10, but showing one corner of the panel turned back to illustrate the upper side of one of the Velcro interlocking fabric fasteners.

FIG. 12 is a diagrammatic front elevation, showing elastic panties, used with the removable crotch panel of FIG. 10, to hold the female urinary collection device on the body of the user.

FIGS. 13 and 14 are rear and side elevational views, showing the elastic panties of FIG. 12.

FIG. 15 is a diagrammatic section, taken generally as indicated by the line 15—15 in FIGS. 12 and 14, looking down into the elastic panties from the top and showing the removable crotch panel with the urine collection receptacle supported thereon.

FIG. 18 is an exploded or disassembled perspective view, showing the assembly of the urinary collection device with the removable crotch panel and a pair of absorbant pads.

FIG. 19 is a fragmentary perspective view showing the assembly of the elastic panties with the removable crotch panel and the absorbant pads.

FIG. 20 is an enlarged elevational section, showing a female urinary collection device with a pessary which is inflated with air or some other similar fluid.

FIG. 20A is a detail view of the inflation site, the view being taken generally as indicated by the line 20A—20A in FIG. 20.

FIG. 25 is a diagrammatic front view of an elastic belt or harness for holding the female urinary collection device in its proper place on the body of the user.

FIG. 26 is a diagrammatic rear view of such harness.

FIG. 27 is a diagrammatic top view of such harness.

FIG. 28 is a diagrammatic side view of such harness.

FIG. 29 is a fragmentary elevational section, taken through the crotch portion of such harness, and showing the manner in which the urinary collection device is supported.

FIG. 30 is a fragmentary top view, taken generally as indicated by the line 30—30 in FIG. 29, and showing the crotch portion of the harness, with the urinary collection device mounted thereon.

FIG. 31 is an enlarged fragmentary section, taken generally along the line 31—31 in FIG. 30.

DETAILED DESCRIPTION OF ILLUSTRATIVE EMBODIMENTS

Figure 16:
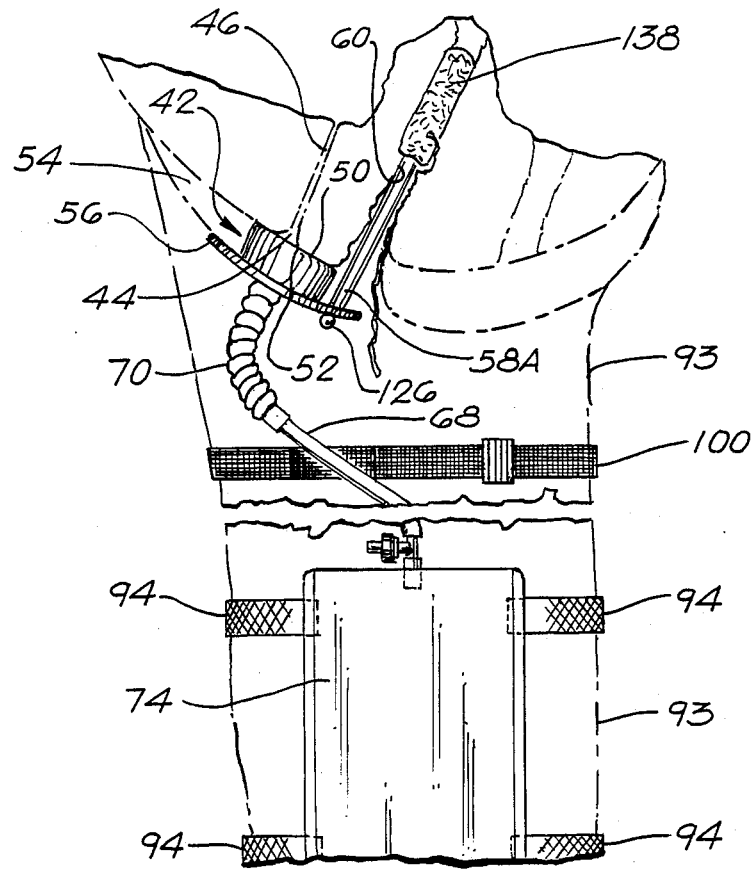
FIG. 16 is a diagrammatic lateral elevational section, showing the female urinary collection device in place on the body of the user.
Figure 17:
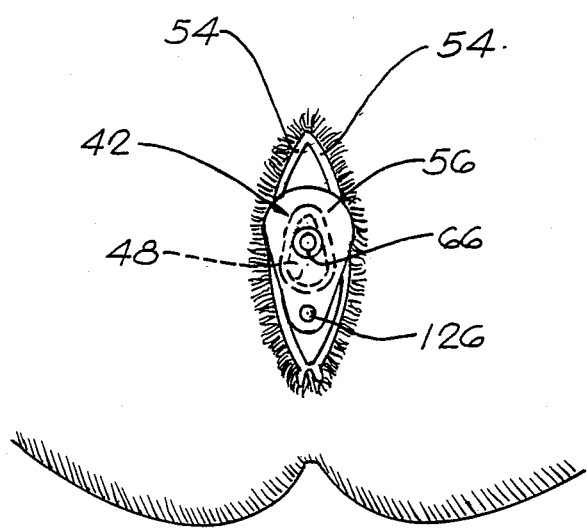
FIG. 17 is a diagrammatic view, looking generally in an upward direction, and showing the female urinary collection device on the body of the user.

FIG. 1 is a general elevational view of a preferred illustrative embodiment of the present invention, in the form of a female urinary collection device 40, including a urine collection receptacle 42, which is generally cup-shaped, as shown in greater detail in FIGS. 2 and 3. As shown in FIG. 16, the receptacle 42 is adapted to receive urine from the mouth or orifice 44 of the female user's urethra 46. The receptacle 42 has a generally annular side wall 48 with a very soft rounded compliant upper lip 50, adapted to form a seal with the user's vestibular tissues 52, around the orifice 44 of the urethra 46. The lip 50 has an initial shape corresponding generally to the contours of the vestibular tissues 52. Moreover, the lip 50 is extremely soft, compliant and resilient and is able to conform itself precisely to the exact contours of the vestibular tissues 52, so as to form a perfect seal, with a minimum of applied pressure between the lip and the vestibular tissues. As shown in FIGS. 16 and 17, the urine collection receptacle 42 fits between the labia majora lip tissues 54 of the user. As an optional but preferred construction, the cup-shaped urine receptacle 42 has a bottom flange portion or plate 56, adapted to engage the lower extremities of the labia majora lip tissues 54, to assist in positioning and stabilizing the urine receptacle 42, relative to the orifice 44 and the vestibular tissues 52.

As another optional but preferred construction, the female urinary collection device 40 has a pessary member 58, adapted to be received in the user's vagina 60, as shown in FIG. 16, whereby the position and orientation of the urine collection receptacle 42 are stabilized and maintained. The pessary member 58 is located to the rear of the urine collection receptacle 42 and may be either permanently secured to the bottom flange plate 56, as shown in FIG. 1, or may be detachably mounted on the bottom flange plate 56, as shown in FIG. 1A, which illustrates a modified pessary member 58A, to be described in greater detail presently.

As shown in FIG. 3, the urine receptacle 42 has a bottom wall portion 62 formed with a drain opening 64 to which a drain tube 66 is connected. The urine flows out of the receptacle 42 through the drain tube 66 and into a drain hose 68 having an extremely flexible section 70, connected to the drain tube 66. Preferably, the flexible section 70 is corrugated or convoluted, as shown in FIG. 1. For the sake of compact illustration, the hose 68 is shown in an S-shaped curve in FIG. 1, but, in actual use, the hose 68 extends downwardly, as shown in FIG. 16, so that the urine flows along the hose 68 by gravity. The lower end of the hose 68 is connected by a coupling assembly 72 to a storage bag 74, or some other suitable receptacle. At its inlet, the bag 74 has an anti-reflux valve 75 inside the bag, to prevent reverse flow of the urine from the bag, back into the coupling assembly 72. The bag 74 is made of resinous plastic film, or some other suitable material. As shown, the bag 74 is adapted to be emptied through a spout 76 having a removable and replaceable closure cap 78. The bag 74 is a disposable item and may be removed, discarded, and replaced with a new bag, as desired.

The flow of urine from the receptacle 42, through the hose 68 and into the flexible bag 74 tends to produce a partial vacuum in the interior of the hose 68, and also in the receptacle 42. It is desirable to provide means for venting or relieving such vacuum, because otherwise, if the vacuum is not relieved, atmospheric pressure may press the urine receptacle 42 against the vestibular tissues of the user, with an uncomfortable amount of force. As shown in FIG. 1, the female urinary collection device 40 is provided with a vacuum relief valve 80. The coupling assembly 72 includes a T-fitting 82 having a side tube 84 to which the vacuum relief valve 80 is connected. The valve 80 is a one-way valve, in that the valve allows atmospheric air to pass through the valve, into the T-fitting 82, while preventing any outflow of urine. As an additional but optional safeguard, the atmospheric air inlet 86 is fitted with a filter holder 88, containing a filter 90 which allows the passage of air while preventing the passage of urine or any other water base liquid. Such filters are well known to those skilled in the art.

Vacuum relief valves, in general, are also known to those skilled in the art, but an especially advantageous vacuum relief valve is disclosed and claimed in the co-pending U.S. patent application of William H. Beecher, Ser. No. 794,517, filed Nov. 4, 1985.

As desired, the closure cap 78 may be removed and replaced with an additional drain hose 91, shown in FIG. 9, adapted to be closed by a shutoff clamp 92 which may be opened to drain the bag 74. The hose 91 may also be connected to a larger night bag.

The urine storage bag 74 may be secured to one leg 93 of the user by means of a pair of straps 94, as shown in FIG. 16. The bag 74 of FIG. 1 has corner flaps 96, formed with slits 98 for receiving the straps 94.

Another strap 100 is preferably employed to hold the lower portion of the hose 68 against the leg 93 of the user, as shown in FIGS. 1 and 16. The arrangement is such that the flexible section 70 of the hose 68 provides for free movement of the leg, without causing shifting movement of the urine receptacle 42, relative to the vestibular tissues 52 of the user.

As shown in FIG. 3, the annular side wall 48 of the urine collection receptacle 42 is hollow and comprises inner and outer shells or walls 102 and 104 which merge smoothly at the rounded upper lip 50. Preferably, the annular side wall 48 is molded in one piece, including the lip 50 and the inner and outer shells 102 and 104. The one-piece molding also preferably includes the bottom wall portion 62 and the drain tube 66 of the urine receptacle 42. The material employed in the one-piece molding is preferably a soft, highly compliant and resilient silicone elastomer, or some other similar synthetic elastomer material. The wall thickness of the lip 50, the inner shell 102 and the outer shell 104 is made small, so that these elements will be very soft and highly compliant.

The space 105 between the inner and outer shells 102 and 104 is filled with a viscous liquid silicone elastomer gum or gel 106, or some other similar synthetic elastomer gum or gel material. With this construction, the annular side wall 48 and the upper lip 50 are very soft and compliant, so that they are able to conform precisely to the exact contours of the user's vestibular tissues 52, around the orifice 44 of the urethra 46, with a minimum of applied pressure between the lip 50 and the vestibular tissues 52.

Due to the provision of the thin silicone lip 50, the thin silicone inner and outer shells 102 and 104, and the viscous liquid silicone gum or gel filling material 106, the lip 50 can be deformed very easily, with a minimum of applied pressure. When the urine receptacle 42 is removed from the user's body, the annular side wall 48 and the lip 50 restore themselves to their original shape.

In the construction of FIG. 3, the hollow space 105 between the inner and outer shells 102 and 104 of the annular side wall 48 is closed and sealed by a bottom closure member or plate 108 which is also preferably made of a silicone elastomer or some other similar synthetic elastomer material. Preferably, the bottom closure plate 108 is bonded to the bottom wall 62 and the inner and outer shells 102 and 104, by using a silicone cement, or some other similar adhesive material. The bottom closure plate 108 is illustrated as having a drain tube shell or stub 110 which surrounds and reinforces the drain tube 66. Again, a silicone adhesive is employed as a bonding agent between the drain tube 66 and the surrounding shell 110, which thus is functionally unified with the drain tube 66. The silicone material employed in the bottom closure plate 108 may be the same as the material employed in the side wall 48 and the bottom wall 62 of the receptacle 42, or may be a somewhat stiffer material with a lesser degree of softness.

In the construction of FIGS. 2 and 3, the bottom flange portion 56 is molded in one piece with the outer shell 104 of the annular side wall 48. As shown in FIG. 2, the bottom flange portion 56 is molded with a multiplicity of ventilating holes 112, extending through the flange portion 56. The provision of such holes 112 is an optional feature, but is desirable, to avoid any accumulation of moisture or body fluids between the flange portion 56 and the labia majora lips 54 of the user.

In tho construction of FIGS. 1, 2 and 3, the pessary 58 is generally cylindrical in shape, with a smoothly rounded tip portion 114, for easy insertion into the user's vagina 60. As shown in FIGS. 2 and 3, the pessary 58 has a thin hollow outer shell 116, preferably made of a silicone elastomer or some other similar synthetic elastomer material, so that the outer shell 116 is very soft, compliant and resilient. The outer shell 116 is filled with a viscous liquid silicone elastomer gum or gel 118, or some other similar synthetic viscous liquid elastomer material. With this construction, the pessary 58 conforms itself precisely to the exact contours of the user's vagina 60. The pessary 58 is very soft, and may be compressed very easily to a smaller diameter, with a corresponding elongation of the pessary.

As shown in FIG. 3, the silicone outer shell 116 is molded in one piece with the outer shell 104 of the annular side wall 48. The hollow space within the outer shell 116, containing the silicone gum or gel 118, is closed by the bottom closure plate 108, which is preferably bonded to the outer shell 116, using a silicone cement or other suitable adhesive. As shown in FIGS. 2 and 3, the bottom flange portion 56 connects with the lower portion of the pessary's outer shell 116 and is bonded to the bottom closure plate 108 by the silicone adhesive. Thus, the bottom closure plate 108 is functionally unified with a portion of the bottom flange 56. The bottom closure plate 108 reinforces the portion of the bottom flange 56 to which the plate 108 is laminated by the use of the silicone cement.

As previously indicated, FIG. 1A illustrates a modified or alternate pessary construction 58A which is detachably mounted on the bottom flange portion 56 of the urine collection receptacle 42. As shown, the pessary 58A and the flange portion 56 are detachably connected together in the manner of poppy beads.

Figure 4:
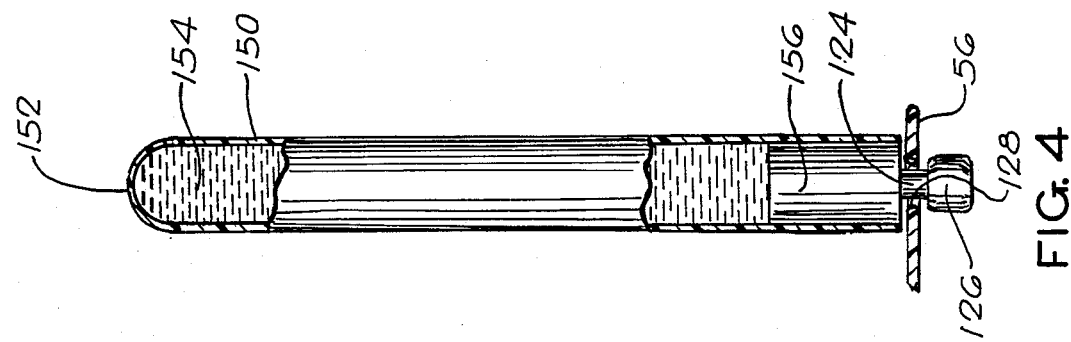
FIG. 4 is an enlarged elevational section, showing a detachable pessary construction, similar to that shown in FIG. 1A, but comprising a thin silicone shell filled with a silicone gum or gel.

FIGS. 4–7 illustrate several alternate detachable pessary constructions, each of which has a connecting or joint member 122 at its lower end. Each connecting member 122 has a downwardly projecting stem or neck portion 124 of reduced diameter, to which a rounded head 126 is connected, having an enlarged diameter, relative to the diameter of the neck portion 124 As shown in FIGS. 2A and 4, the enlarged head or ball 126 is adapted to be forced through a slightly smaller opening 128 in the bottom flange portion 56 of the urine collection receptacle 42. There is an interference fit between the enlarged head 126 and the opening 128. Due to the fact that the bottom flange portion 56 is made of a soft resilient silicone elastomer or the like, as previously indicated, the enlarged head 126 can be forced through the undersize opening 128, without any great difficulty, with a snap or pop action. The neck portion 124 is significantly smaller in diameter than the opening 128, so as to afford a small amount of free play between the detachable pessary 58A and the bottom flange portion 56. Such play allows the pessary 58A to assume the desired angle for easy insertion into the user's vagina 60. The pessary 58A can be detached from the bottom flange portion 56, without any great difficulty, by forcing the enlarged head 126 upwardly through the undersize opening 128, but the detachable joint is sufficiently secure to avoid accidental detachment of the pessary 58A.

The provision of a detachable pessary makes it possible to use the female urinary collection device, with or without a pessary, as desired. Moreover, a variety of different pessary constructions may be provided, to suit the needs or desires of various users. Several different pessary constructions are shown in FIGS. 1A, 1B and 4–7.

Figure 6:
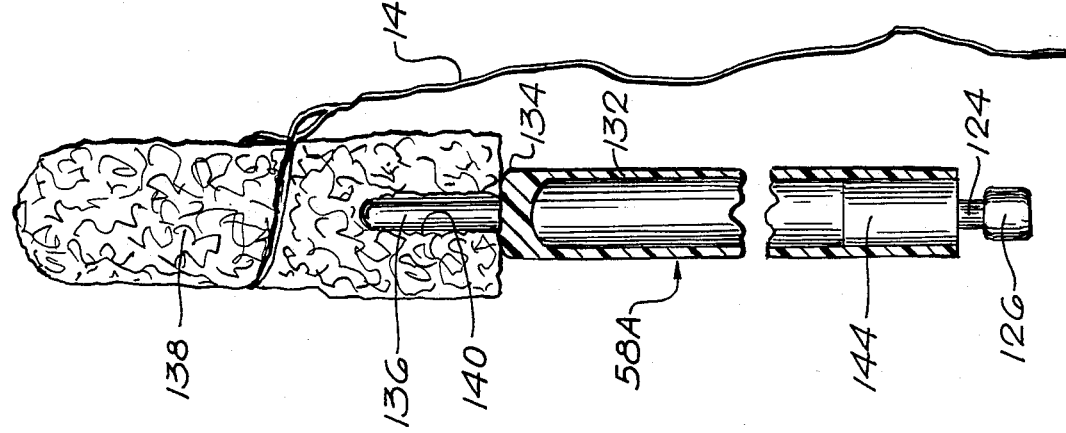
FIG. 6 is a view similar to FIG. 5, but showing a tampon mounted on the pessary.
Figure 5:
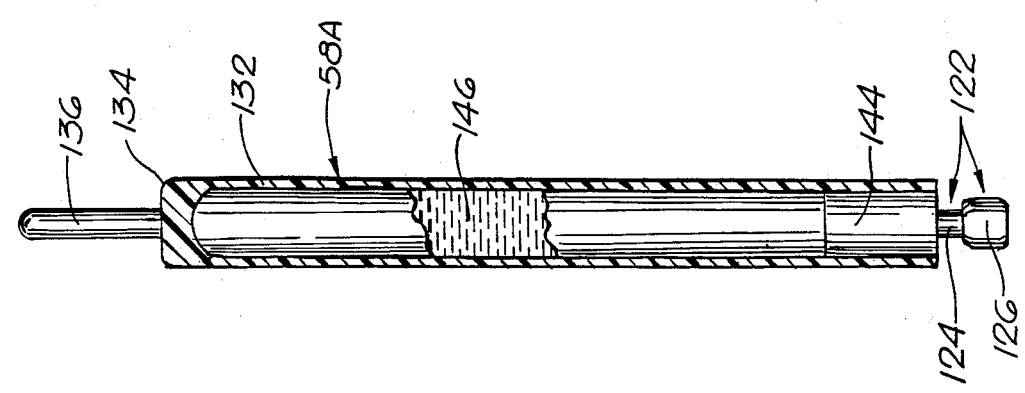
FIG. 5 is an enlarged elevational section showing an alternate detachable pessary construction, adapted to receive a tampon, as in FIG. 1A, but comprising a thin silicone shell filled with a silicone gum or gel.

The detachable pessary 58A, as shown in FIGS. 1A, 5 and 6, has a hollow tubular body member 132 with a closed upper end portion 134, formed with a reduced axial pin 136 for receiving and supporting a tampon 138, as shown in FIG. 6. The tampon 138 is of a well known construction, having an axial opening 140, adapted to receive the rounded pin 136. More commonly, the opening 140 is employed to receive an applicator rod, but in this case, the opening 140 is used to receive the supporting pin 136 on the tubular pessary member 132. The tampon 138 has the usual string or strings 142 for removing the tampon from the user's vagina opening 60.

The lower end of the tubular pessary member 132, as shown in FIGS. 5 and 6, is fitted with a cylindrical closure member 144, molded in one piece with the neck member 124 and the enlarged head or ball 126.

The tubular pessary member 132 is preferably made of a soft compliant silicone elastomer, or some other similar material, so that the member 132 will be soft, compliant and resilient to a high degree. Preferably, the closure member 144 is also made of a silicone elastomer and is bonded within the tubular member 132 by using a silicone cement or some other suitable adhesive.

As a desirable option, the tubular pessary member 132 is preferably filled with a viscous liquid silicone gum or gel 146, or some similar material, which is contained in the tubular member 132 by the cylindrical closure member 144.

FIG. 4 illustrates a modified pessary 148 which is substantially the same as the pessary 58 of FIG. 1, except that the pessary 148 is detachably mounted on the bottom flange member 56, in the manner previously described. Thus, the pessary 148 has a thin-walled tubular outer shell 150 with a smoothly rounded tip portion 152. The outer shell 150 is very soft, compliant and resilient, and is preferably made of a soft silicone elastomer, or some similar material. The outer shell 150 is filled with a viscous liquid silicone gum or gel 154, or some similar material.

At its lower end, the tubular outer shell 150 is closed by a cylindrical insert 156, preferably bonded to the outer shell 150 by using a silicone cement or some other suitable adhesive. The cylindrical insert 156 is molded in one piece with the reduced neck member 124 and the enlarged head or ball 126, for detachably connecting the pessary 148 to the bottom flange member 56, in the manner previously described.

The pessary 148 of FIG. 4 has all of the advantages of the pessary 58, shown in FIG. 1. In addition, the pessary 148 is detachably mounted on the bottom flange member 56 of the female urinary collection device, so that the pessary 148 may be used or not, at the option of the user. Moreover, the detachable pessary 148 may be supplied in a variety of sizes, to suit the needs or desires of various users. However, a single size can be used comfortably by most if not all users, because the pessary 148, with its filling material 154 made of silicone gum or gel, is so soft, compliant and resilient, and thus is so very capable of conforming itself to the contours of the user's vagina 60.

Figure 7:
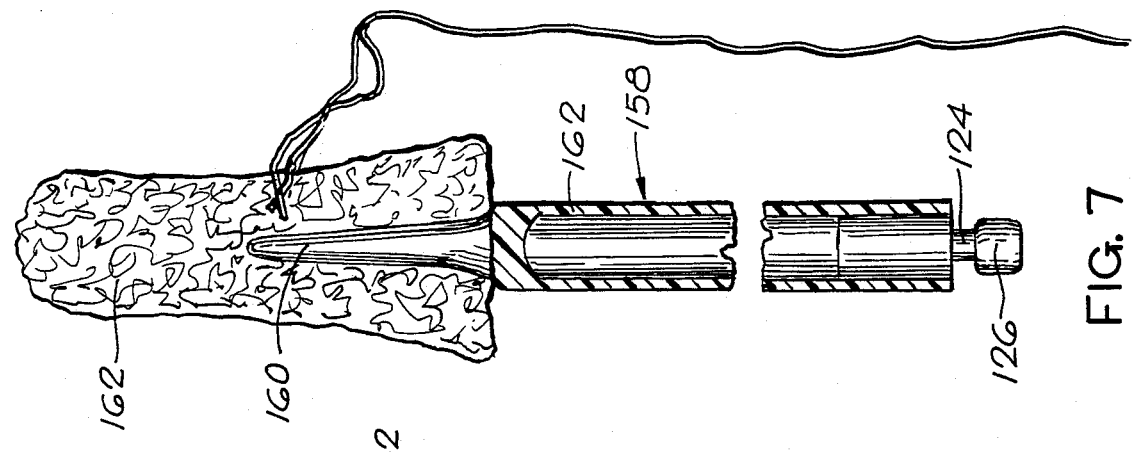
FIG. 7 is another view similar to FIG. 5, but showing a slightly modified pessary with a different type of tampon mounted thereon.

FIG. 7 illustrates another detachable pessary 158, which is substantially the same as the detachable pessary 58A of FIGS. 5 and 6, except that the outer end of the pessary 158 is formed with a tapered pin 160, replacing the pin 136, for receiving and holding a tulip-shaped tampon 162, which represents another well known tampon construction. The detachable pessary 158 has a hollow tubular body 162, molded in one piece with the pin 160. The body 162 is otherwise the same as the body 132. The hollow tubular body 162 is shown without any filling material, but may optionally be filled with a viscous liquid silicone gum or gel.

FIG. 1B illustrates another detachable pessary 166 which is detachably connected to the bottom flange member 56, as previously described in connection with FIGS. 1A, 2A and 4–7. Thus, the pessary 166 has the same enlarged head 126 as previously described and illustrated, adapted to be forced through the undersize opening 128 in the bottom flange 56. The pessary 166 is illustrated as a slightly curved, generally cylindrical rod having a smoothly rounded tip 168, for easy insertion into the user's vagina 60. In this case, the pessary 166 is preferably solid, rather than hollow, but is made of a soft flexible resilient silicone elastomer, or some similar synthetic elastomer. The pessary 166 may be molded in one piece with the enlarged head 126 and the connecting neck portion 124, which may be the same as illustrated in FIGS. 4–7.

FIGS. 10–15 show elastic panties or briefs 172 for holding the female urinary collection device 40 against the body of the user. To facilitate the installation and removal of the urinary collection device 40, the panties 172 preferably have a removable crotch panel 174 for covering a slot or opening 176 in the panties. The removable crotch panel 174 is particularly advantageous for installing and removing the urinary collection device 40, when the user is bedridden. As to a bedridden patient, it is much easier to remove and replace the removable crotch panel 174, than to remove and replace the elastic panties 172. Both the panties 172 and the removable crotch panel 174 may be made of an elastic fabric material. The crotch panel 174 is mounted against the outside of the panties 172 and is removably held in place by suitable means, such as the illustrated interlocking fabric pads 178. It will be understood that each of the pads 178 has a pair of interlocking fabric elements, one mounted on the removable crotch panel 174 and the other mounted on the elastic panties 172. The interlocking elements adhere together rather securely, but can be pulled apart quite easily, when the crotch panel 174 is to be removed.

As shown in FIG. 10, the removable crotch panel 174 is formed with an elongated slot 182 which is sufficiently large to provide for the insertion of the entire urine collection receptacle 42, including the bottom flange 56 and the pessary 58, through the slot 182. After such initial insertion, only the drain tube 66 and the flexible section 70 of the hose 68 extend through the slot 182. To insure that the crotch panel 174 will retain the bottom flange portion 56 of the urine collection receptacle 42, the crotch panel 174 is provided with a closure flap 184 which partially closes the slot 182. The closure flap 184 is detachably retained in its closed position by suitable means, such as the illustrated interlocking fabric pads 186 and 188, on the crotch panel 174 and the closure flap 184.

When installed, the urine collection receptacle 42 is pressed gently into its position of use by the removable elastic crotch panel 174 of the elastic panties 172. The soft annular lip 50 of the receptacle 42 is pressed gently against the user's vestibular tissues 52, around the orifice 44 of the urethra 46. The bottom flange portion 56 is pressed gently against the lower extremities of the labia majora lips 54.

During installation of the female urinary collection device 40, the pessary 58 or 58A is inserted into the user's vagina 60. If the user is having a menstrual flow, the detachable pessary 58A and the tampon 138 are used. Alternatively, the detachable pessary 158 and the tampon 162 may be used. If the use of a pessary is not desired, the detachable pessary 58A may be removed. However, the use of the pessary 58 or 58A has the advantage of stabilizing the position and orientation of the urine collection receptacle 42, so that it is more reliably retained in sealing engagement with the user's vestibular tissues 52 around the orifice 44 of the urethra 46.

FIGS. 18 and 19 illustrate the further option of providing one or more absorbant pads 190 between the removable crotch panel 174 and the bottom flange 56 of the female urinary collection device 40. Two such pads 190 are provided in the assembly of FIGS. 18 and 19. The illustrated pads 190 are in the form of standard small size sanitary napkins of the self-adhesive type. For this particular application, each of the pads 190 is formed with a central opening 192 and a slit 194 which connects with the opening 192. In each case, the opening 192 is adapted to receive the flexible hose portion 70. The slit 194 is large enough to provide for the insertion of the urine collector assembly, comprising the receptacle 42, the bottom flange 56, and the pessary 58, 58A or 58B. The absorbant pads 190 are assembled in their final positions, between the bottom flange portion 56 and the removable crotch panel 174, with the slits 194 extending in opposite directions from the openings 192, through which the flexible hose portion 70 extends. The absorbant pads 190 serve the purpose of absorbing any small amount of urine which may leak out of the urine collection receptacle 42, if it momentarily becomes unseated from the user's vestibular tissues 52, around the orifice 44 of the urethra 46.

Figure 21:
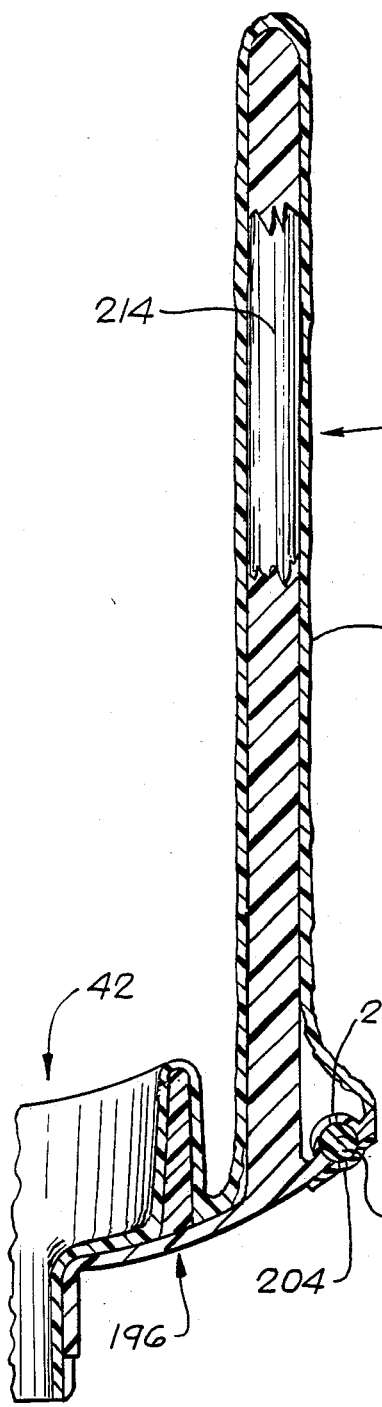
FIG. 21 is a fragmentary sectional view, similar to FIG. 20, but showing the pessary in a partially deflated condition, for easy insertion into the vaginal opening.
Figure 24:
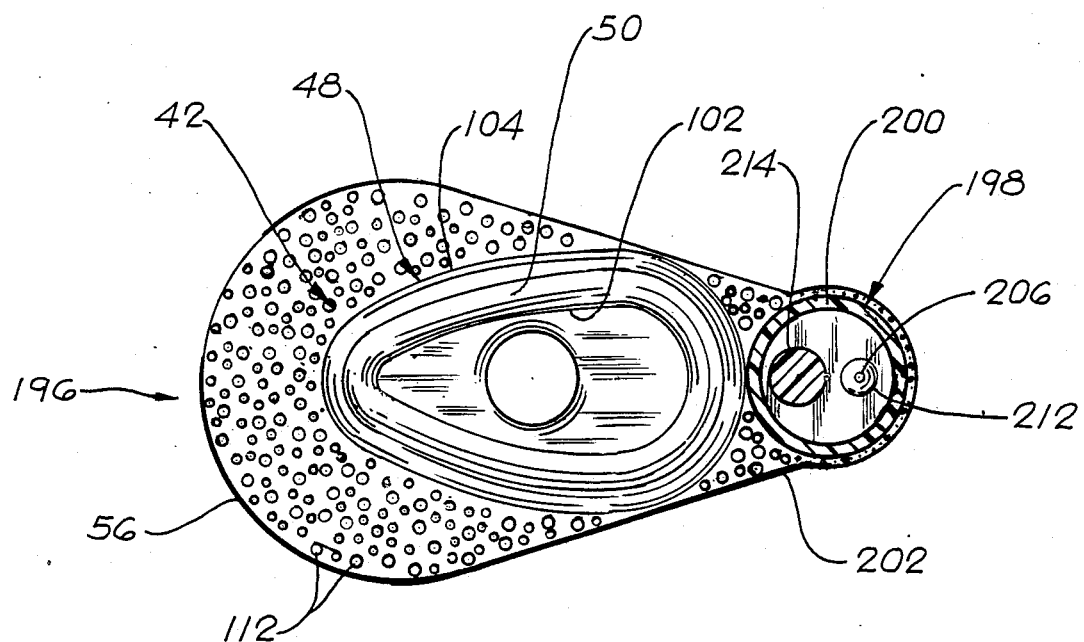
FIG. 24 is a section, taken generally along the line 24—24 in FIG. 20.

FIGS. 20, 20A, 21 and 24 illustrate a modified female urinary collection device 196 which is the same as the device 40 of FIGS. 1, 2 and 3, except that the gum or gel filled pessary 58 is replaced with an inflatable pessary 198, shown inflated in FIGS. 20 and 24, while being shown deflated in FIG. 21. The inflatable pessary 198 has a thin-walled generally tubular outer shell 200 which is closed at its upper end by a smoothly rounded tip portion 202. At its lower end, the outer shell 200 is preferably molded in one piece with the annular side wall 48 of the urine receptacle 42, and thus is made of a very soft compliant resilient silicone elastomer or some similar material. The lower end of the outer shell 200 is closed by an extension 202 of the bottom plate 108, preferably bonded to the outer shell 200 by the use of a silicone cement or some other suitable adhesive.

The device 196 includes means for introducing and withdrawing an inflating fluid, into and out of the outer shell 200. The inflating fluid is usually air, but may be any other suitable gas or gaseous mixture, or any suitable liquid, such as water, for example. As to the illustrated device 196 of FIGS. 20 and 20A, the inflation fluid is introduced and withdrawn by inserting a hollow hypodermic needle, not shown, through a pair of aligned inflation ports 204 and 206 which are closed initially by a ball or mass 208, made of a self-healing gum material, preferably a silicone elastomer gum. The illustrated gum ball 208 is retained between half shells 210 and 212, in which the ports 204 and 206 are formed. As shown, the half shell 212 is molded in one piece with the bottom closure member 202, while the half shell 210 is bonded to the bottom closure member 202 by the use of a silicone cement, or some other suitable adhesive. Self-healing inflation devices of this general type are known, and the construction of the device may be varied in accordance with known or suitable technology.

Preferably, the inflatable pessary 198 is inserted in a deflated condition, as shown in FIG. 21, into the user's vagina 60. The pessary 198 is then moderately inflated, to afford better retention in the vagina 60, while maintaining the complete comfort of the user. When inflated, the thin outer shell 200 conforms itself to the contours of the vagina 60.

To provide for easy insertion of the pessary 198 in a deflated condition, as shown in FIG. 21, the pessary 198 is preferably provided with an internal stiffening member 214, illustrated as a soft flexible generally cylindrical rod with a smoothly rounded tip 216. Preferably, the stiffening rod 214 is molded in one piece with the bottom closure member 202 and is made of a soft resilient silicone elastomer, or some other similar material.

The small amount of air pressure needed to inflate the outer shell 200 of the pessary 198 may be provided by any suitable means, such as a hand pump, not shown, which may utilize a hollow resilient compressible bulb, of the type commonly used on hand operated syringes.

Figure 22:
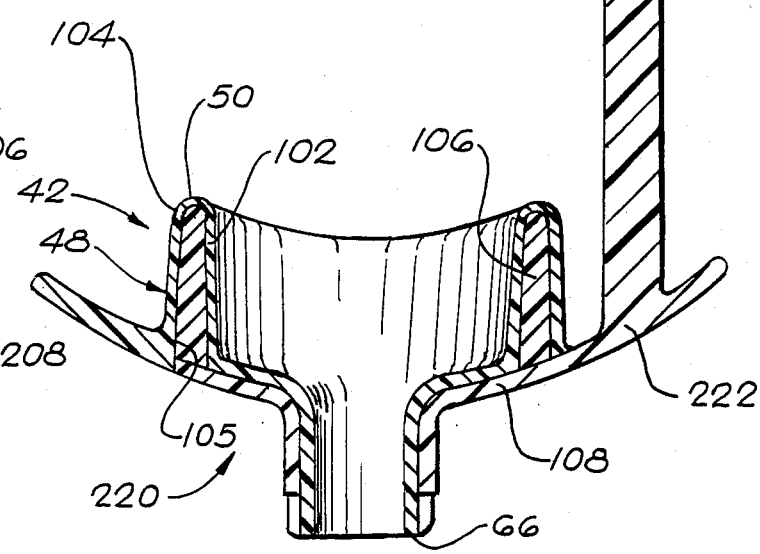
FIG. 22 is a view similar to FIG. 20, but showing a female urinary collection device with a solid flexible pessary.

FIG. 22 illustrates another modified female urinary collection device 220 which is similar to the device 196 of FIG. 20, except that the inflatable outer shell 200 is omitted, leaving the soft compliant resilient cylindrical member 214 to serve as a pessary, which is molded in one piece with an extension 222 of the bottom closure plate 108. Thus, the pessary 214, the extension 222 and the bottom closure plate 108 are molded in one piece from a soft resilient silicone elastomer, or some other similar synthetic elastomer material. The device 220 of FIG. 22 does not utilize the inflation port elements 204–212 of FIG. 20. Except as otherwise described, the female urinary collection device 220 of FIG. 22 may be the same as the device 40 of FIGS. 1, 2 and 3.

Figure 23:
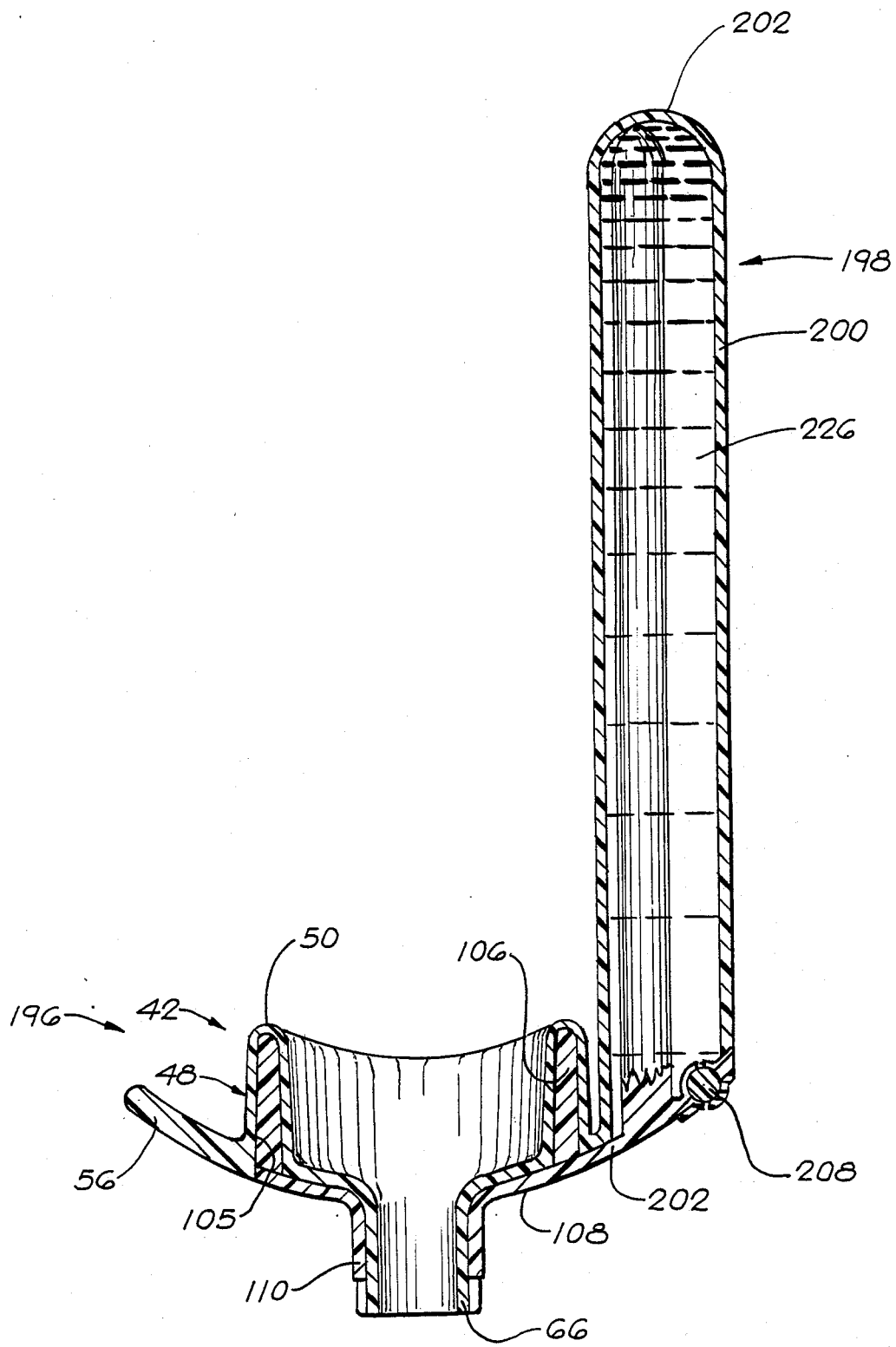
FIG. 23 is a view similar to FIG. 20, but showing the pessary filled with a viscous liquid elastomer, such as a silicone gum or gel.

FIG. 23 shows the female urinary collection device 196, which is the same as illustrated in FIGS. 20 and 24, except that the hollow outer shell 200 of the inflatable pessary 198 is inflated or filled with a liquid 226, which may be water, as previously described, but may alternatively be a viscous liquid silicone elastomer gum or gel, introduced by means of a hollow hypodermic needle through the self-healing gum ball 208, as previously described in connection with FIG. 20. The silicone gum or gel 226 is left in place permanently. Moreover, the amount of the gum or gel 226 is closely controlled so that the outer shell 200 is inflated to only such a moderate extent that it is easy to insert and remove the pessary 198, into and out of the user's vagina 60. The provision of the silicone gum or gel 226 as a filling material produces a pessary which is very soft and compliant, and which is easy to compress to a smaller diameter, for very easy insertion into the user's vagina 60.

When the pessary 198 is to be filled with a viscous liquid silicone gum or gel, the outer shell 200 is first preferably evacuated by pumping out air through a hollow hypodermic needle, inserted through the self-healing gum ball 208. The silicone gum or gel is then introduced into the outer shell 200 through a hollow hypodermic needle, in the manner previously described. This procedure avoids the formation of air bubbles or pockets in the viscous liquid gum or gel, within the outer shell 200.

FIGS. 25–31 illustrate modified means 227 for holding the female urinary collection device 40 in its proper position on he user's body 228, such means 227 being in the form of an elastic harness, comprising an elastic waistband 230, a flexible crotch panel 232, front elastic harness straps 234, extending between the front portion of the waistband 230 and the front portion of the crotch panel 232, and rear elastic harness straps 236, extending between the rear portion of the waistband 230 and the rear portion of the crotch panel 232.

The waistband 230 and the harness straps 234 and 236 are made of a suitable elastic fabric, of the general type commonly employed in athletic supporters, garter straps and the like. The crotch panel 232 is preferably made of a suitable fabric, which does not need to be elastic, but can be elastic, if desired. The straps 234 and 236 are preferably sewn to the crotch panel 232, while also being sewn to the elastic waistband 230.

As shown in FIG. 29, the crotch panel 232 is formed with an opening 238, through which the flexible hose section 70 is inserted. As shown in FIGS. 25–31, the female urinary collection device 40 is the same as illustrated in FIGS. 1, 2 and 3. The urine collection receptacle 42 and the bottom flange member 56 are supported by the upper side of the crotch panel 232, while the flexible hose section 70 extends downwardly through the opening 238. As shown in FIGS. 29–31, a disposable absorbant pad 240 may be interposed between the bottom flange member 56 and the crotch panel 232, to absorb any small amount of urine which may leak between the urine receptacle 42 and the user's vestibular tissues 52. Such pad 240 may be in the form of a sanitary napkin, having a standard well known construction, except that the pad 240 is formed with an opening 242, through which the drain tube 66 and the flexible hose section 70 are inserted. The pad 240 may be of the self-sticking type, having a pressure sensitive adhesive applied to portions of one side. As shown most clearly in FIG. 31, the adhesive 244 is downwardly directed and is employed for detachably sticking the pad 240 to a plastic or other waterproof facing 246, laminated to the upper side of the crotch panel 232. The facing 246 may be in the form of a resinous plastic film, suitably secured to the crotch panel 232 on its upper side, as by sewing or by the use of a suitable adhesive. From time to time, the disposable absorbant pad 240 may be removed and replaced with a new pad, as needed.

It is easy for the user, or those assisting her, to put on and remove the elastic harness 227. The front and rear elastic harness straps 234 and 236 apply a firm but gentle pressure between the soft annular lip 50 of the urine receptacle 42 and the user's vestibular tissues 52, around the orifice 44 of the urethra 46. The elastic harness straps 234 and 236 also apply a gentle pressure between the bottom flange member 56 and the lower extremities of the user's labia majora lips 54.

When the female urinary collection device 40 is installed, the soft compliant pessary 58 is inserted into the user's vagina 60, as previously described.

The provision of the pessary is an optional feature, as previously indicated. If a pessary is not desired, the user may be supplied with a modified urinary collection device, similar to the device 40, but without the pessary 58. The user may also be supplied with a female urinary collection device having a detachable pessary, as described in connection with FIGS. 1A, 1B, 2A and 4–7.

As previously indicated, the thin flexible walls or shells 102 and 104 of the urine receptacle 42, as well as the thin outer wall 116 of the pessary 58, are preferably made of a soft compliant silicone elastomer. These thin walls are shown in FIGS. 1–3. The same or similar silicone elastomer materials may be employed in molding the thin pessary walls 132, 150 and 162 of FIGS. 4–7, and the thin pessary wall 200 of FIGS. 20, 21, 23 and 24. The silicone elastomer materials employed in these thin flexible walls are generally quite soft. The commercially available elastomer materials have an approximate hardness range from 25 to 90 on the Shore A durometer scale. Elastomers within this range are operative in the device of the present invention. However, it is preferable to employ an elastomer material having a hardness near the lower or softer end of this range. Thus, under typical conditions, it is believed that the best results are obtained with a durometer (Shore A) of approximately 36. However, by changing wall thicknesses and/or cross sections, higher durometer (harder) materials may be used.

The same silicone elastomer materials may be employed in the bottom closure member 108 of FIG. 3, the rod-like pessary 166 of FIG. 1B, and the rod-like pessary member 214 of FIGS. 20–24. The same hardness or durometer range applies, from 25 to 90 (Shore A). To facilitate production and to achieve the maximum economy, it is advantageous to use the same material for all of the solid silicone elastomer components. However, under typical conditions, it is believed that the best results are achieved by using a slightly harder silicone elastomer, having a durometer of approximately 45, for the bottom closure member 108 and the rod-like pessary members 166 and 214.

As previously indicated, viscous liquid silicone gum or gel elastomer materials may be employed as the filling material 106 for the urine receptacle 42 and as the filling material 118 for the pessary 58 of FIGS. 2 and 3. Substantially the same materials may be employed as the filling materials 146 and 154 of FIGS. 4 and 5, and as the filling material 226 of FIG. 23. These viscous liquid silicone gum or gel materials have the characteristic of plasticity, in that they have the capability of flowing under moderate pressures. The plasticity or flow characteristics of silicone gum and silicone gel elastomer materials are generally stated in terms of penetration or sag test values.

The commercially available silicone gum elastomer materials have an approximate penetration range (Williams) of 50 to 6,000. In the present invention, the working range is approximately 250 to 6,000. The recommended gum material is near the higher penetration (softer) end of the range. Thus, under typical conditions, it is believed that the best results are achieved with a penetration value of approximately 5,700 (Williams).

The commercially available silicone gel elastomer materials have an approximate range from a penetration of 4.0 millimeters, at the hard end of the range, using a Universal Penetrometer with a 69.5 gram load on a 6.35 millimeter diameter aluminum shaft, to a sag test of 8 centimeters sag (minimum) after 30 minutes, at the soft end of the scale. The recommended gel material should have characteristics near the higher penetration and sag test (softer) end of the range. Thus, under typical conditions, it is believed that best results are obtained by using a soft silicone gel material having a penetration of approximately 5 millimeters, using a Universal Penetrometer with a 19.5 gram load on a 6.35 millimeter diameter aluminum shaft. However, by changing cross sections and/or thicknesses, lower penetration materials may be used.

Figure 32:
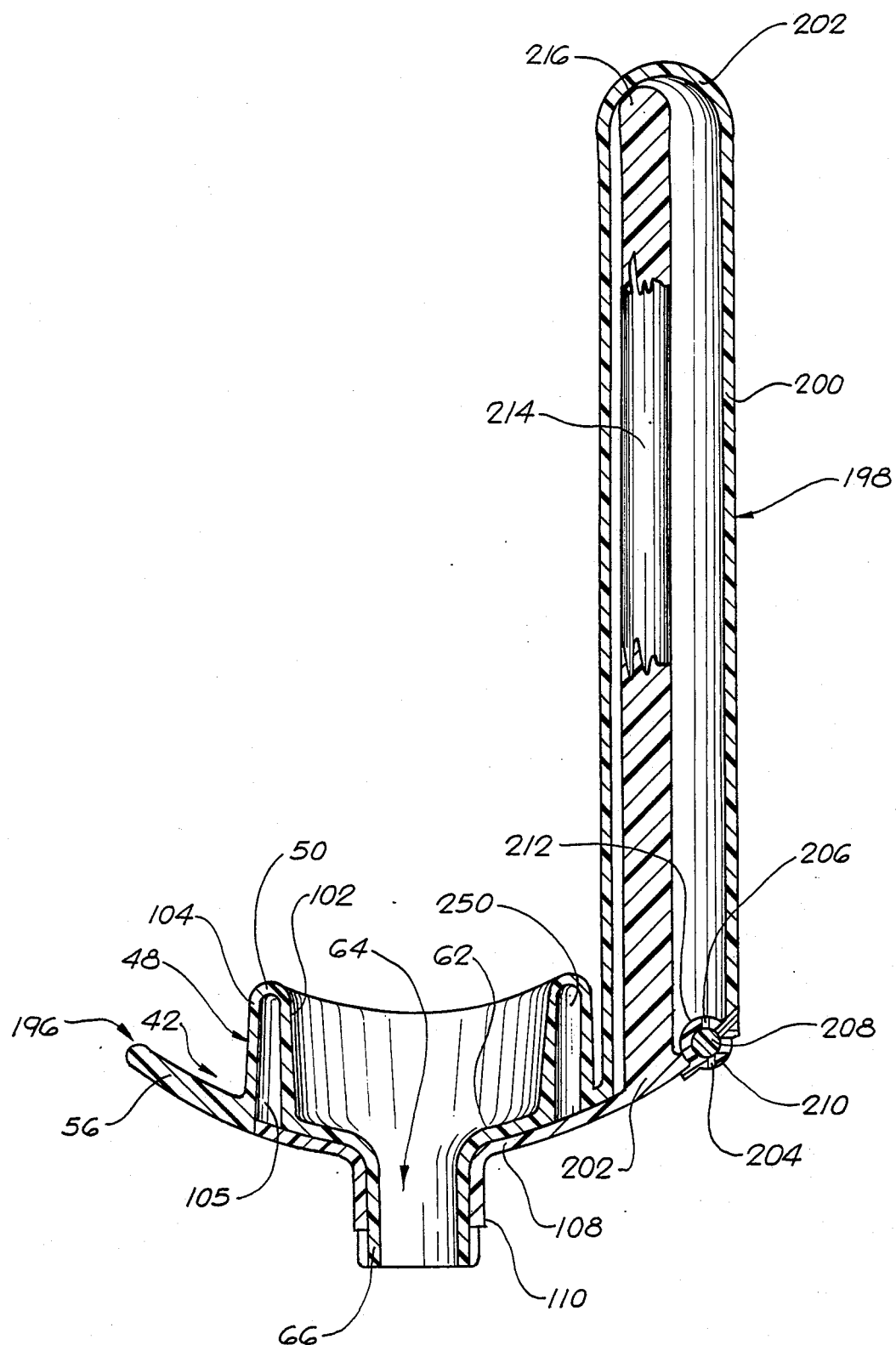
FIG. 32 is an enlarged elevational section, similar to FIG. 20, but showing a modified female urinary collection device in which the space within the device is filled with air or some other suitable gaseous material.

In the various embodiments of the present invention, the urinary collection receptacle 42 may be modified by filling the sealed space 105 in the annular side wall 48 with suitable alternate fluids, other than elastomer gums or gels. As shown in FIG. 32, for example, the space 105 may be filled with air 250, or some other suitable gas or gaseous mixture, such as nitrogen, for example. The air or other gas should be substantially at or somewhat above atmospheric pressure; for example, from zero to approximately five pounds per square inch above atmospheric pressure.

Air or some other suitable gas is an advantageous filling material for the sealed space 105, because the softness and compliance of the side wall 48 and the lip 50 are maintained, so that the lip 50 adapts itself to the shape of the vestibular tissues 52 around the user's urethra orifice 44, whereby a perfect seal is established and maintained with such tissues. When the urine receptacle 42 is removed from the user's body, the air or other gas assists in restoring the urine receptacle to its original shape. The use of air as the filling material for the space 105 facilitates the manufacture of the urine receptacle 42.

Figure 33:
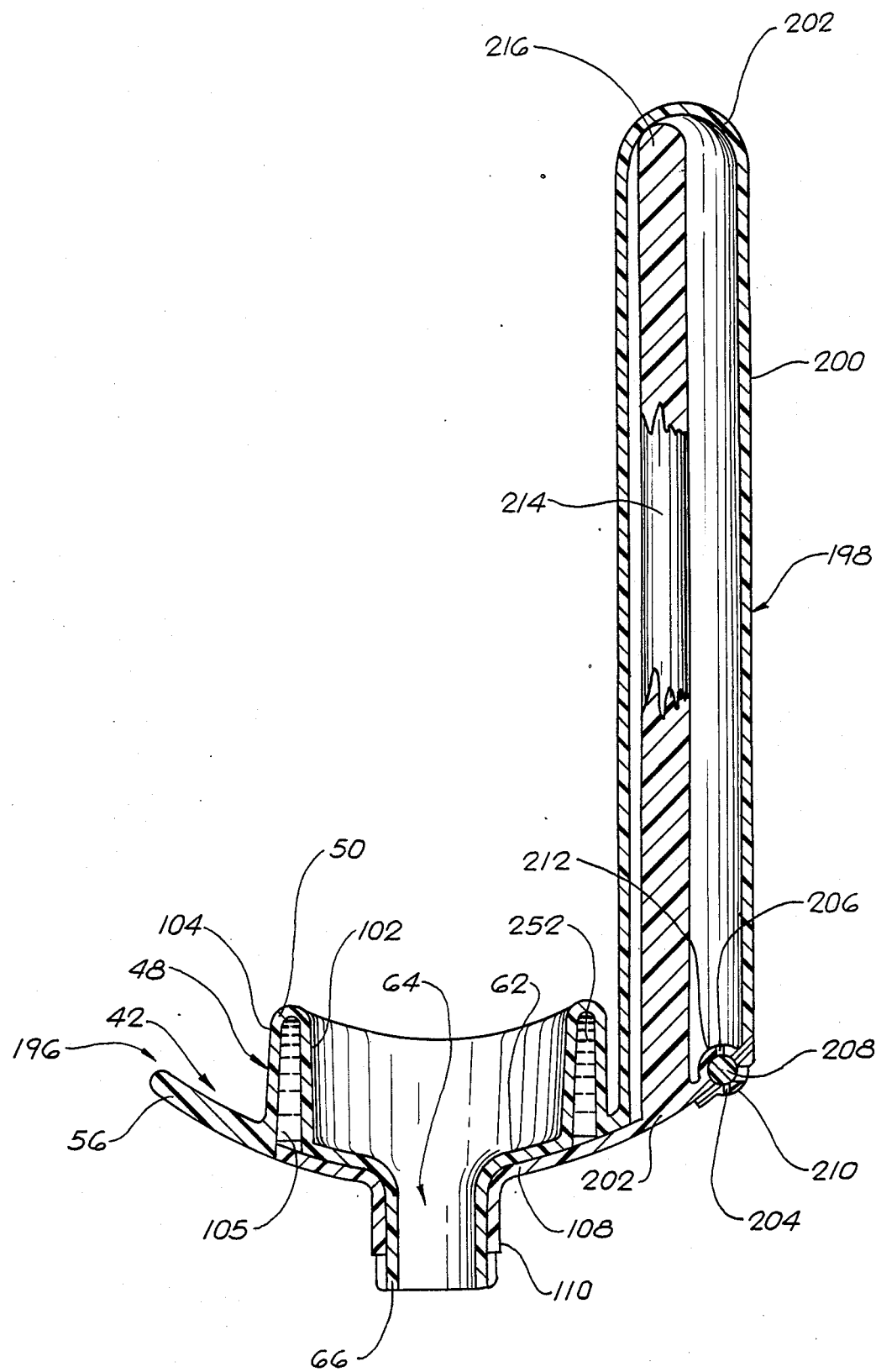
FIG. 33 is an enlarged elevational section, similar to FIG. 20, but showing another modified female urinary collection device, in which the space within the device is filled with water or some other suitable liquid.

As shown in FIG. 33, the space 105 in the side wall 48 of the urine receptacle 42 may be filled with other alternate fluids, including suitable liquids 252, such as water, particularly sterile water, or normal saline solution. Such liquids are low in cost and readily available. With such suitable liquids as the filling material for the sealed space 105, the lip 50 is still able to conform itself to the contours of the user's vestibular tissues 52 around the urethra Orifice 44, because of the softness, compliance and resilience of the thin lip 50 and the thin walls 102 and 104. Other suitable liquids may be employed as the filling material for the sealed space 105.

I claim:

1. A female urinary collection device, comprising
a generally cup-shaped receptacle for collecting urine from the urethra orifice of a female user,
said receptacle having a bottom wall portion and a generally annular side wall portion projecting generally upwardly therefrom and terminating in a soft rounded compliant generally annular lip portion for sealing engagement with the external vestibular tissues of the user immediately around the urethra orifice and between the labia majora lips of the user,
said side wall portion being of a size corresponding generally with the space between the labia majora lips of the user to fit comfortably between the labia majora lips,
and a drain tube portion connecting with the bottom wall portion for draining the urine out of the receptacle,
the side wall portion being hollow and comprising spaced inner and outer shells merging at their upper extremities to form said rounded lip portion,
the inner and outer shells being made of a soft thin highly flexible compliant synthetic elastomer material,
said side wall portion having a hollow space between substantially the entire extent of said inner and outer shells,
said hollow space being filled with a viscous liquid synthetic elastomer material enabling said lip portion to conform precisely with the exact contours of the vestibular tissues of the user immediately around the urethra orifice with a minimum of pressure between said lip portion and the vestibular tissues.

2. A device according to claim 1,
including a bottom flange plate constituting a direct extension of said bottom wall portion and projecting laterally therefrom for engaging the lower extremities of the external labia majora lip portions of the user to assist in stabilizing the position of the receptacle and to limit pressure between the lip portion of the receptacle and the vestibular tissues of the user.

3. A device according to claim 2,
including means wearable by the user for pressing the flange plate lightly against the user's external labia majora lip portions.

4. A device according to claim 2,
including elastic fabric panties wearable by the user for pressing said flange plate against the lower extremities of the external labia majora lip portions of the user and thereby lightly pressing the cup-shaped receptacle against the user's vestibular tissue immediately around the orifice of the urethra,
said panties having a crotch portion access slot therein located for positioning opposite the orifice of the urethra,
the panties having a detachable crotch panel made of soft flexible fabric for selectively closing and opening said slot to provide for installing and removal of said receptacle,
said crotch panel and said crotch portion having fastening means for detachable fastening said crotch panel to said crotch portion,
said detachable crotch panel having an opening therein for receiving the drain tube while also having selectively operable closure means for partially closing said opening.

5. A device according to claim 2,
including a pessary member mounted directly on said flange plate for insertion into the vagina of the user to stabilize the position of the device.

6. A device according to claim 5,
in which such pessary member includes a detachable mounting connection to the flange portion.

7. A device according to claim 5,
in which the pessary member is hollow and has a thin outer wall with a space therein,
such thin outer wall being made of a flexible highly compliant synthetic elastomer material,
and a viscous liquid synthetic elastomer material filling the space within the thin outer wall of the pessary member whereby the pessary member conforms itself to the contours of the user's vagina.

8. A device according to claim 5,
in which the pessary member is hollow and has a thin flexible compliant outer wall with a space therein,
said outer wall of said pessary member being mounted directly onto said flange plate,
a stiffening member mounted directly on said flange plate and disposed within said last-mentioned space for initial insertion of the pessary member,
and inflation means mounted on said flange plate for admitting a pressurized fluid to the space within the pessary member for inflating the pessary member after insertion whereby the pessary member conforms itself to the contours of the user's vagina.

9. A device according to claim 5,
in which the pessary member is hollow and has a thin outer wall with a space therein,
such thin outer wall being made of a soft flexible highly compliant silicone elastomer material,
and a viscous liquid silicone gum material filling the space within the thin outer wall of the pessary member whereby the pessary member conforms itself to the contours of the user's vagina.

10. A device according to claim 5,
in which the pessary member is hollow and has a thin outer wall with a space therein,
such thin outer wall being made of a soft flexible highly compliant silicone elastomer material,
and a viscous liquid silicone elastomer gel filling the space within the thin outer wall of the pessary member whereby the pessary member conforms itself to the contours of the user's vagina.

11. A device according to claim 10,
in which the thin highly flexible compliant synthetic elastomer material of said receptacle and said pessary member is a silicone elastomer material,
the viscous liquid synthetic elastomer material of said receptacle and said pessary member being a silicone elastomer gum with flow characteristics defined by an approximate penetration range (Williams) of 250 to 6,000 from the hard end of the range to the soft end.

12. A device according to claim 10,
in which the thin highly flexible compliant synthetic elastomer material of said receptacle and said pessary member is a silicone elastomer material,
the viscous liquid synthetic elastomer material being a silicone elastomer gel with flow characteristics having an approximate range from a penetration of 4.0 millimeters, at the hard end of the range, using a Universal Penetrometer with a 69.5 gram load on a 6.35 millimeter diameter aluminum shaft, to a sag test of 8 centimeters sag (minimum) after 30 minutes, at the soft end of the scale.

13. A device according to claim 10,
in which the thin highly flexible compliant synthetic elastomer material of said receptacle and said pessary member is a silicone elastomer material,
the viscous liquid synthetic elastomer material of said receptacle and said pessary member being a soft silicone elastomer gum with flow characteristics defined by a penetration value of approximately 5,700 (Williams).

14. A device according to claim 10,
in which the thin highly flexible compliant synthetic elastomer material of said receptacle and said pessary member is a silicone elastomer material,
the viscous liquid synthetic elastomer material of said receptacle and said pessary member being a soft silicone elastomer gel with flow characteristics defined by a penetration of approximately 5 millimeters, using a Universal Penetrometer with a 19.5 gram load on a 6.35 millimeter diameter aluminum shaft.

15. A device according to claim 1,
including a bottom flange plate constituting a direct extension of said bottom wall portion and projecting laterally therefrom for engaging the lower extremities of the external labia majora lip portions of the user to assist in stabilizing the position of the receptacle and to limit pressure between the lip portion of the receptacle and the vestibular tissues of the user,
said bottom flange plate being formed with a multiplicity of ventilating openings therethrough to provide for the escape of moisture.

16. A device according to claim 1,
in which the thin highly flexible compliant synthetic elastomer material is a silicone elastomer material,
the viscous liquid synthetic elastomer material being a silicone elastomer gum.

17. A device according to claim 1,
in which the thin highly flexible compliant synthetic elastomer material is a silicone elastomer material,
the viscous liquid synthetic elastomer material being a silicone elastomer gel.

18. A device according to claim 1,
in which the thin highly flexible compliant synthetic elastomer material is a silicone elastomer material,
the viscous liquid synthetic elastomer material being a silicone elastomer gum with flow characteristics defined by an approximate penetration range (Williams) of 250 to 6,000 from the hard end of the range to the soft end.

19. A device according to claim 1,
in which the thin highly flexible compliant synthetic elastomer material is a silicone elastomer material,
the viscous liquid synthetic elastomer material being a silicone elastomer gel with flow characteristics having an approximate range from a penetration of 4.0 millimeters, at the hard end of the range, using a Universal Penetrometer with a 69.5 gram load on a 6.35 millimeter diameter aluminum shaft, to a sag test of 8 centimeters sag (minimum) after 30 minutes, at the soft end of the scale.

20. A device according to claim 1,
in which the thin highly flexible compliant synthetic elastomer material is a silicone elastomer material,
the viscous liquid synthetic elastomer material being a soft silicone elastomer gum with flow characteristics defined by a penetration value of approximately 5,700 (Williams).

21. A device according to claim 1,
in which the thin highly flexible compliant synthetic elastomer material is a silicone elastomer material,
the viscous liquid synthetic elastomer material being a soft silicone elastomer gel with flow characteristics defined by a penetration of approximately 5 millimeters, using a Universal Penetrometer with a 19.5 gram load on a 6.35 millimeter diameter aluminum shaft.

22. A female urinary collection device, comprising
a generally cup-shaped receptacle for collecting urine from the urethra orifice of a female user,
said receptacle having a bottom wall portion and a generally annular side wall portion connecting directly therewith and projecting upwardly therefrom and terminating in a soft rounded compliant generally annular lip portion for sealing engagement with the external vestibular tissues of the user immediately around the urethra orifice and between the labia majora lips of the user,
said side wall portion being of a size corresponding generally with the space between the labia majora lips of the user to fit comfortably between the labia majora lips,
a drain tube portion connecting with the bottom wall portion for draining the urine out of the receptacle,
the side wall portion being hollow and comprising spaced inner and outer shells merging at their upper extremities to form said rounded lip portion,
the inner and outer shells being made of a soft thin highly flexible compliant synthetic elastomer material,
said side wall portion having a hollow space between substantially the entire extent of said inner and outer shells,
said hollow space being filled with a viscous liquid synthetic elastomer material enabling said lip portion to conform precisely with the exact contours of the vestibular tissues of the user immediately around the urethra orifice with a minimum of pressure between said lip portion and the vestibular tissues,
said receptacle having a rearward extension in the form of a flange plate constituting a direct rearward extension of said bottom wall portion,
and a pessary member mounted directly on said rearward extension for insertion into the user's vagina to stabilize the position of the receptacle.

23. A device according to claim 22,
in which such pessary member includes a detachable mounting connection to the rearward extension.

24. A device according to claim 22,
in which the pessary member is hollow and has a thin outer wall with a space therein,
such thin outer wall being made of a soft flexible highly compliant synthetic elastomer material,
and a viscous liquid synthetic elastomer material filling the space within the thin outer wall of the pessary member whereby the pessary member conforms itself to the contours of the user's vagina.

25. A female urinary collection device, comprising a generally cup-shaped receptacle for collecting urine from the urethra orifice of a female user, said receptacle having a bottom wall portion and a generally annular side wall portion connecting directly therewith and projecting upwardly therefrom and terminating in a soft rounded compliant generally annular lip portion for sealing engagement with the external vestibular tissues of the user immediately around the urethra orifice and between the labia majora lips of the user, said side wall portion being of a size corresponding generally with the space between the labia majora lips of the user to fit comfortably between the labia majora lips, a drain tube portion connecting with the bottom wall portion for draining the urine out of the receptacle, the side wall portion being hollow and comprising spaced inner and outer shells merging at their upper extremities to form said rounded lip portion, the inner and outer shells being made of a soft thin highly flexible compliant silicone elastomer material, said side wall portion having a hollow space between substantially the entire extent of said inner and outer shells, said hollow space being filled with a viscous liquid silicone elastomer material enabling said lip portion to conform precisely with the exact contours of the vestibular tissues of the user immediately around the urethra orifice with a minimum of pressure between said lip portion and the vestibular tissues, a bottom flange plate constituting a direct extension of said bottom wall portion and projecting laterally and rearwardly therefrom for engaging the lower extremities of the external labia majora lip portions of the user to assist in stabilizing the position of the receptacle and to limit pressure between the lip portion of the receptacle and the vestibular tissues of the user, said bottom flange plate being made of a soft flexible silicone elastomer material, and a soft flexible pessary member mounted directly on said bottom flange plate for insertion into the vagina of the user to stabilize the position of the receptacle, said pessary member being made of a soft flexible silicone elastomer material.

26. A device according to claim 25, in which such pessary member includes a detachable mounting connection to the bottom flange portion.

27. A device according to claim 25, in which the pessary member is hollow and has a thin outer wall with a space therein, such thin outer wall being made of a soft flexible highly compliant silicone elastomer material, and a viscous liquid silicone elastomer material filling the space within the thin outer wall of the pessary member whereby the pessary member conforms itself to the contours of the user's vagina.

28. A female urinary collection device, comprising a generally cup-shaped receptacle for collecting urine from the urethra orifice of a female user, said receptacle having a bottom wall portion and a generally annular side wall portion connecting directly therewith and projecting generally upwardly therefrom and terminating in a soft rounded compliant generally annular lip portion for sealing engagement with the external vestibular tissues of the user immediately around the urethra orifice and between the labia majora lips of the user, said side wall portion being of a size corresponding generally with the space between the labia majora lips of the user to fit comfortably between the labia majora lips, and a drain tube portion connecting with the bottom wall portion for draining the urine out of the receptacle, the side wall portion being hollow and comprising spaced inner and outer shells merging at their upper extremities to form said rounded lip portion, the inner and outer shells being made of a soft thin highly flexible compliant synthetic elastomer material, said side wall portion having a hollow space between substantially the entire extent of said inner and outer shells, a bottom flange plate connecting directly with said bottom wall portion of said receptacle and projecting laterally outwardly therefrom for engaging the lower extremities of the external labia majora portions of the user to assist in stabilizing the position of the receptacle and to limit pressure between the lip portion of the receptacle and the vestibular tissues of the user, said bottom flange plate being made of a soft flexible synthetic elastomer material, said hollow space being filled with a fluid enabling said lip portion to conform precisely with the exact contours of the vestibular tissues of the user immediately around the urethra orifice with a minimum of pressure between said lip portion and the vestibular tissues.

29. A device according to claim 28, in which such fluid takes the form of a gas.

30. A device according to claim 28, in which such fluid takes the form of air.

31. A device according to claim 18, in which said fluid takes the form of a liquid.

32. A device according to claim 28, in which such fluid takes the form of water.

33. A device according to claim 28, in which such fluid takes the form of a normal saline solution.

34. A device according to claim 28, in which such fluid takes the form of a soft silicone gum elastomer material.

35. A device according to claim 18, in which said fluid takes the form of a soft silicone gel elastomer material.

* * * * *

UNITED STATES PATENT AND TRADEMARK OFFICE
CERTIFICATE OF CORRECTION

PATENT NO. : 4,889,533
DATED : December 26, 1989
INVENTOR(S) : William H. Beecher It is certified that error appears in the above-indentified patent and that said Letters Patent is hereby corrected as shown below:

Column 15, claim 4, line 57 and 58, change "tissue" to --tissues--.
                line 59, after "portion" insert --with a crotch--.

Column 20, claim 28, line 25, before "hollow" insert --sealed--.
          claim 31, line 48, change "18" to --28--.
          claim 35, line 57, change "18" to --28--

In the title on the title page, insert "FLUID-" before "FILLED" so that the title will read "FEMALE URINARY COLLECTION DEVICES HAVING HOLLOW-WALLED FLUID-FILLED URINE RECEPTACLES."

Signed and Sealed this

Twenty-fifth Day of January, 1994

Attest:

BRUCE LEHMAN

*Attesting Officer*     *Commissioner of Patents and Trademarks*